United States Patent [19]

Suzuki et al.

[11] Patent Number: 5,039,694
[45] Date of Patent: Aug. 13, 1991

[54] SUBSTITUTED-AMIDO COMPOUNDS AND PHYTOPATHOGENIC FUNGICIDES CONTAINING THE SAME

[75] Inventors: Hideo Suzuki; Takeshi Mita; Toshiaki Takeyama, all of Funabashi; Yoshinori Ochiai, Minamisaitama; Masami Hanaue, Minamisaitama; Masao Nishikubo, Minamisaitama; Kazuhiro Yamagishi, Minamisaitama, all of Japan

[73] Assignee: Nissan Chemical Industries, Ltd., Tokyo, Japan

[21] Appl. No.: 344,895

[22] Filed: Apr. 28, 1989

Related U.S. Application Data

[63] Continuation-in-part of Ser. No. 116,215, Nov. 3, 1987, abandoned.

[30] Foreign Application Priority Data

Nov. 6, 1986 [JP] Japan .................................. 61-264763
Apr. 28, 1987 [JP] Japan .................................. 62-103044
May 28, 1987 [JP] Japan .................................. 62-133048

[51] Int. Cl.$^5$ .................... A01N 43/56; C07D 231/12
[52] U.S. Cl. ...................................... 514/406; 548/374
[58] Field of Search ......................... 548/374; 514/406

[56] References Cited

U.S. PATENT DOCUMENTS 4,432,784  2/1984  Kay et al. ............................ 546/284
4,500,536  2/1985  Yoshida et al. ...................... 548/374
4,508,731  4/1985  Riebli et al. ........................ 548/374
4,515,959  5/1985  Kay et al. ............................ 548/374
4,663,341  5/1987  Jacobson ............................. 548/379
4,792,565  12/1988  Shimotori et al. ................... 514/406

FOREIGN PATENT DOCUMENTS 2190375  11/1987  United Kingdom ................ 514/406

Primary Examiner—C. Warren Ivy
Assistant Examiner—Zinna Northington-Davis
Attorney, Agent, or Firm—Oliff & Berridge

[57] ABSTRACT

Disclosed are substituted-amido derivatives of a general formula (I):

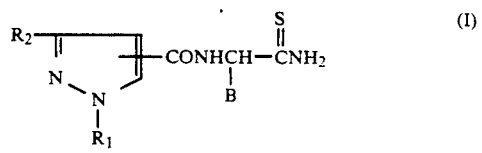

in which $R_1$ represents a group as specifically defined herein; $R_2$ represents a hydrogen atom, a methyl group, a methoxy group or a halogne atom; B represents a 5-membered hetero-aromatic group as specifically defined herein, as well as a method for preparation of the said derivatives and a fungicide containing the said derivative as an active ingredient.

5 Claims, No Drawings

SUBSTITUTED-AMIDO COMPOUNDS AND PHYTOPATHOGENIC FUNGICIDES CONTAINING THE SAME

This is a continuation-in-part of U.S. patent application Ser. No. 07/116,215, filed Nov. 3, 1987, now abandoned.

BACKGROUND OF THE INVENTION

1. Field of the Invention

The present invention relates to new substituted-amido derivatives, method for preparation of the derivatives and fungicides for agricultural and horticultural use containing the same as an active ingredient.

2. Description of the Prior Art

One important problem in agricultural production, especially in culture of fruit trees and vegetables, includes diseases caused by phytopathogenic fungi of Phycomycetes (for example, Pseudoperonospora-caused diseases, Phytophthora-caused diseases, etc.). The diseases caused by these fungi are known to be difficult to protect against because of the special physiological and biological properties of the fungi, and therefore, the development of accepted chemical agents capable of protecting against the fungi is desirable. The extent of damage caused by the fungi of Pseudoperonospora or Phytophthora is great as broadly covering various crops, and the damage is extremely serious.

At present, captan (common name), captafol (common name), dithiocarbamate fungicides (for example, zineb (common name), etc.), chlorothalonil (common name), etc. are being widely used against diseases caused by phytopathogenic fungi of Phycomycetes. However, these fungicides are essentially for the purpose of prevention of diseases and could not almost be expected to have a curative effect, and therefore, these have a fatal defect in that these could not display a sufficient effect when they are applied to diseased plants. A fungicide of an acylalanine series compound, which has recently been developed, for example, metalaxyl (common name), etc., has both a preventive effect and a curative effect. However, tolerant fungi against the fungicide were already present, and therefore, the protective effect of the fungicide has become fairly lowered.

Hitherto, substituted-amido acetonitrile derivatives, substituted-amido thioacetamide derivatives and substituted-amido N-acylthioacetamide derivatives, which are considered to be similar to the compounds of the present invention in view of chemical structures, have already been reported in Japanese Patent Application Laid-Open Nos. 167978/82 (U.S. Pat. No. 4,432,784), 69866/83 (U.S. Pat. No. 4,515,959) and 255759/85 (the term "OPI" as herein referred to means a "published unexamined Japanese patent application"). However, the prior art cannot be said sufficient to provide any practical fungicides for agricultural and horticultural use, and in particular, the known compounds would impart some chemical phytotoxicity against crops, which is one serious outstanding problem.

SUMMARY OF THE INVENTION

One object of the present invention is to provide new amido-substituted derivatives having a fungicidal activity.

Another object of the present invention is to provide a method for preparation of the amido-substituted derivatives.

Still another object of the present invention is to provide a fungicide which has both a preventive effect and a curative effect against diseases caused by phytopathogenic fungi of Phycomycetes (for example, Pseudoperonospora-caused diseases, Phytophthora-caused diseases, etc.) and which does not impart any chemical phytotoxicity against crops.

A further object of the present invention is to provide a method for protection against phytopathogenic fungi by the use of the above-mentioned amido-substituted derivatives.

These and other objects and many of the attendant advantages of this invention will be readily appreciated as the same becomes better understood by reference to the following detailed description.

DETAILED DESCRIPTION OF THE INVENTION

The present inventors earnestly studied the above-mentioned amido-derivatives in order to overcome the above problems, and as a result, have found that the compounds as represented by the following formula (I) have both a preventive effect and a curative effect against Pseudoperonospora-caused diseases, Phytophthora-caused diseases, etc. of various plants with an extremely low chemical phytotoxicity against crops, as the characteristic feature thereof, and therefore have achieved the present invention. The compounds of the present invention are new compounds which are not described in any publications up to the present.

Specifically, the present invention provides new amide derivatives of a general formula (I):

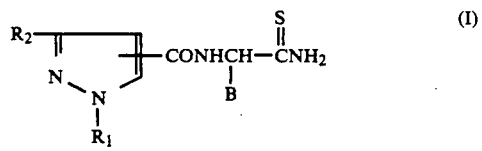

in which $R_1$ represents an alkyl group having from 1 to 10 carbon atoms, a cycloalkyl group having from 3 to 10 carbon atoms, a cycloalkyl alkyl group having from 4 to 10 carbon atoms, an alkenyl group having from 2 to 10 carbon atoms, a cycloalkenyl group having from 3 to 10 carbon atoms, an alkynyl group having 2 to 10 carbon atoms, a halogenated alkyl group having from 1 to 10 carbon atoms, a halogenated cycloalkyl alkyl group having from 4 to 10 carbon atoms, an alkoxyalkyl group having from 2 to 10 carbon atoms, substituted or unsubstituted epoxide having from 2 to 10 carbon atoms, substituted or unsubstituted oxethane having from 3 to 10 carbon atoms, substituted or unsubstituted tetrahydrofuran having from 4 to 10 carbon atoms, substituted or unsubstituted tetrahydrothiophene having from 4 to 10 carbon atoms, substituted or unsubstituted epoxide alkyl having from 3 to 10 carbon atoms, substituted or unsubstituted oxetane alkyl having from 4 to 10 carbon atoms, or substituted or unsubstituted tetrahydrofuran alkyl having from 5 to 10 carbon atoms; and $R_2$ represents a hydrogen atom, a methyl group, a methoxy group or a halogen atom; and B represents

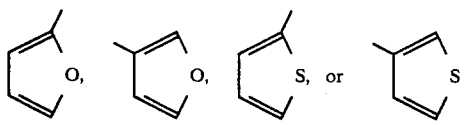

Among the compounds of the present invention, especially preferred compounds are concretely mentioned hereinafter.

(1) No. 766
1,3-Dimethyl-N-[3-thienyl(thiocarbamoyl)methyl]-1H-pyrazole-5-carboxamide

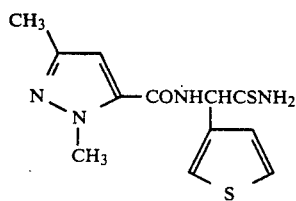

(2) No. 1086
1-Ethyl-3-methyl-N-[2-thienyl(thiocarbamoyl)-methyl]-1H-pyrazole-5-carboxamide

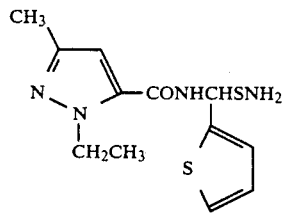

(3) No. 1092
1-Isopropyl-3-methyl-N-[2-thienyl(thiocarbamoyl)-methyl]-1H-pyrazole-5-carboxamide

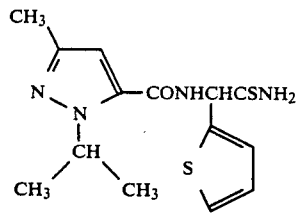

(4) No. 1123
1-Cyclopropylmethyl-3-methyl-N-[2-thienyl(thiocarbamoyl)methyl]-1H-pyrazole-5-carboxamide

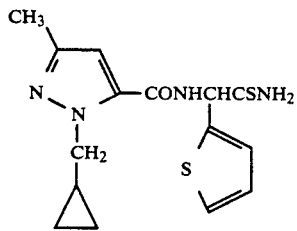

(5) No. 1094
1-Isopropyl-3-methyl-N-[3-thienyl(thiocarbamoyl)-methyl]-1H-pyrazole-5-carboxamide

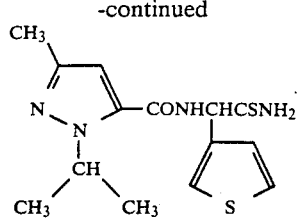

(6) No. 1091
1-Isopropyl(-3-methyl-N-[2-furyl(thiocarbamoyl)-methyl]-1H-pyrazole-5-carboxamide

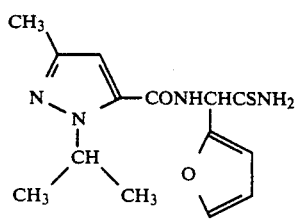

(7) No. 1093
1-Isopropyl-3-methyl-N-[3-furyl(thiocarbamoyl)-methyl]-1H-pyrazole-5-carboxamide

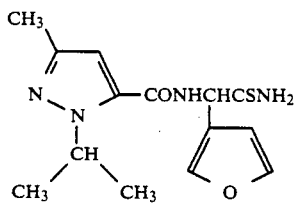

(8) No. 825
1-Ethyl-3-methyl-N-[3-thienyl(thiocarbamoyl)-methyl]-1H-pyrazole-5-carboxamide

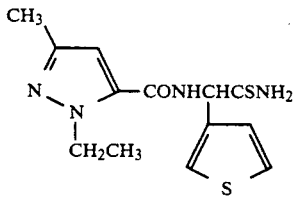

(9) No. 1085
1-Ethyl-3-methyl-N-[2-furyl(thiocarbamoyl)-methyl]-1H-pyrazole-5-carboxamide

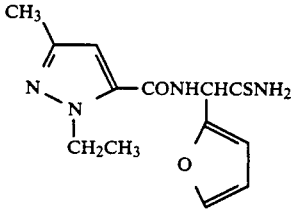

(10) No. 824
1-Ethyl-3-methyl-N-[3-furyl(thiocarbamoyl)-methyl]-1H-pyrazole-5-carboxamide

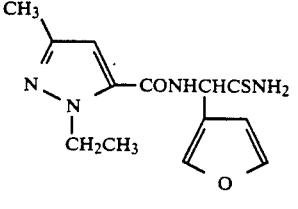

(11) No. 92

-continued 1,3-Dimethyl-N-[2-thienyl(thiocarbamoyl)-methyl]-1H-pyrazole-5-carboxamide

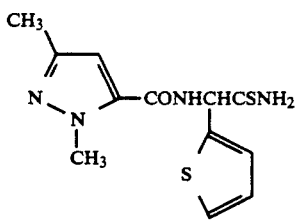

(12) No. 1125
1-Cyclopropylmethyl-3-methyl-N-[3-thienyl-(thiocarbamoyl)methyl]-1H-pyrazole-5-carboxamide

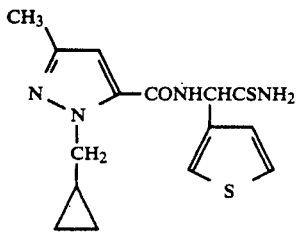

(13) No. 1122
1-Cyclopropylmethyl-3-methyl-N-[2-furyl-(thiocarbamoyl)methyl]-1H-pyrazole-5-carboxamide

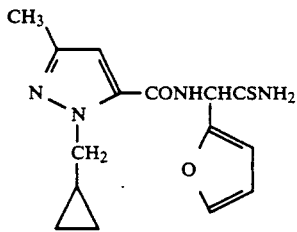

(14) No. 1124
1-Cyclopropylmethyl-3-methyl-N-[3-furyl-(thiocarbamoyl)methyl]-1H-pyrazole-5-carboxamide

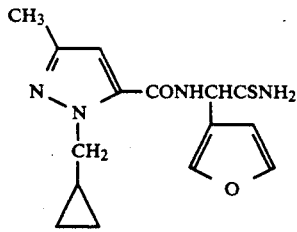

(15) No. 1154
1-Cyclopropyl-3-methyl-N-[3-furyl-(thiocarbamoyl)methyl]-1H-pyrazole-5-carboxamide

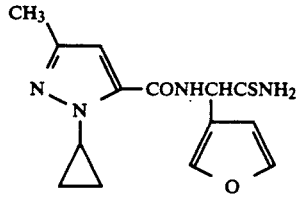

(16) No. 1157
1-Cyclobutyl-3-methyl-N-[3-furyl-(thiocarbamoyl)]-1H-pyrazole-5-carboxamide

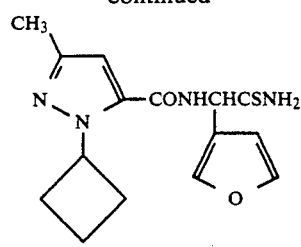

(17) No. 1158
1-Cyclobutyl-3-methyl-N-[3-thienyl-(thiocarbamoyl)methyl]-1H-pyrazole-5-carboxamide

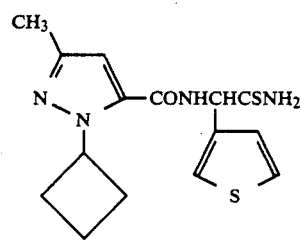

(18) No. 1156
1-Cyclobutyl-3-methyl-N-[2-furyl-(thiocarbamoyl)methyl]-1H-pyrazole-5-carboxamide

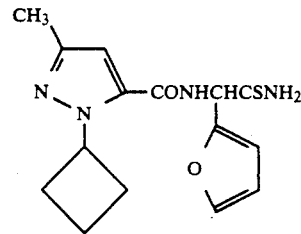

(19) No. 1118
1-Cyclobutyl-3-methyl-N-[2-thienyl-(thiocarbamoyl)methyl]-1H-pyrazole-5-carboxamide

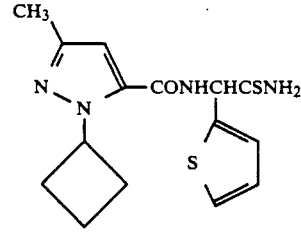

(20) No. 1160
1-Cyclopentyl-3-methyl-N-[3-furyl-(thiocarbamoyl)methyl]-1H-pyrazole-5-carboxamide

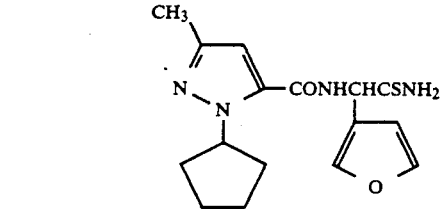

(21) No. 1161
1-Cyclopentyl-3-methyl-N-[3-thienyl-(thiocarbamoyl)methyl]-1H-pyrazole-5-carboxamide

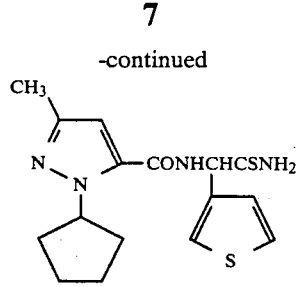

(22) No. 1159
1-Cyclopentyl-3-methyl-N-[2-furyl-(thiocarbamoyl)methyl]-1H-pyrazole-5-carboxamide

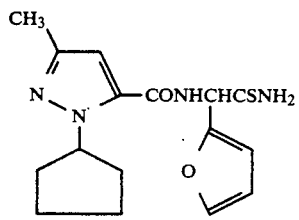

(23) No. 1119
1-Cyclopentyl-3-methyl-N-[2-thienyl(thiocarbamoyl)methyl]-1H-pyrazole-5-carboxamide

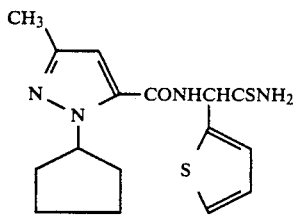

(24) No. 1163
1-Cyclohexyl-3-methyl-N-[3-furyl(thiocarbamoyl)methyl]-1H-pyrazole-5-carboxamide

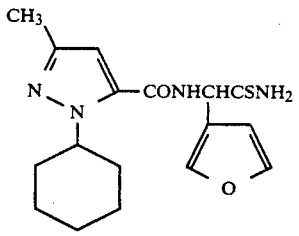

(25) No. 1164
1-Cyclohexyl-3-methyl-N-[3-thienyl-(thiocarbamoyl)methyl]-1H-pyrazole-5-carboxamide

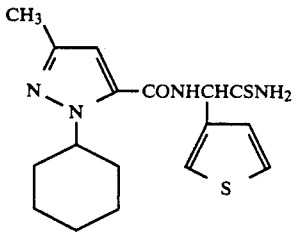

(26) No. 1162
1-Cyclohexyl-3-methyl-N-[-furyl(thiocarbamoyl)methyl]-1H-pyrazole-5-carboxamide

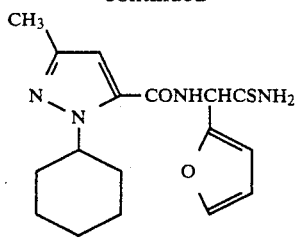

(27) No. 1120
1-Cyclohexyl-3-methyl-N-[2-thienyl(thiocarbamoyl)methyl]-1H-pyrazole-5-carboxamide

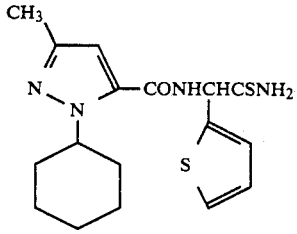

(28) No. 1175
1-(2,3-epoxypropyl)-3-methyl-N-[3-furyl(thiocarbamoyl)methyl]-1H-pyrazole-5-carboxamide

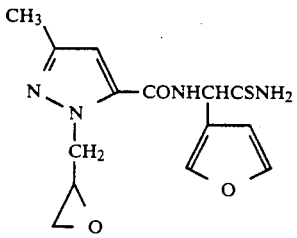

(29) No. 1176
1-(2,3-epoxypropyl)-3-methyl-N-[3-thienyl(thiocarbamoyl)methyl]-1H-pyrazole-5-carboxamide

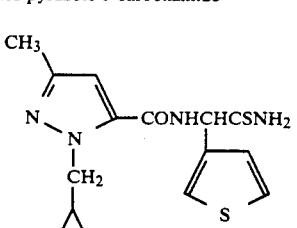

(30) No. 1173
1-(2,3-epoxypropyl)-3-methyl-N-[2-furyl(thiocarbamoyl)methyl]-1H-pyrazole-5-carboxamide

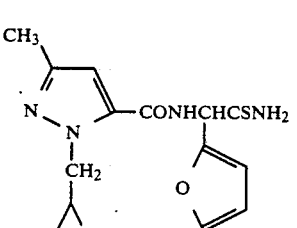

(31) No. 1174
1-(2,3-epoxypropyl)-3-methyl-N-[2-thienyl(thiocarbamoyl)methyl]-1H-pyrazole-5-carboxamide

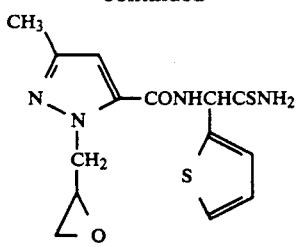

(32) No. 1337
1-(3-tetrahydrothienyl)-3-methyl-N-[2-furyl(thiocarbamoyl)methyl]-1H-pyrazole-5-carboxamide

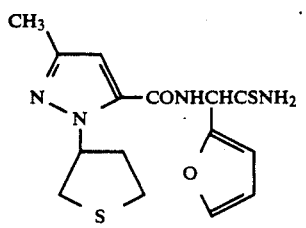

(33) No. 1348
1-(3-cyclopentenyl)-3-methyl-N-[3-thienyl(thiocarbamoyl)methyl]-1H-pyrazole-5-carboxamide

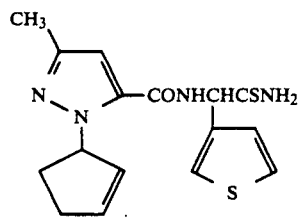

(34) No. 1153
1-cyclopropyl-3-methyl-N-[2-furyl-(thiocarbamoyl)methyl]-1H-pyrazole-5-carboxamide

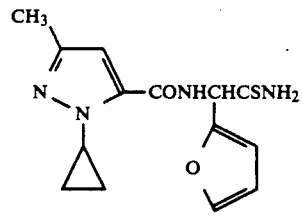

(35) No. 1117
1-cyclopropyl-3-methyl-N-[2-thienyl-(thiocarbamoyl)methyl]-1H-pyrazole-5-carboxamide

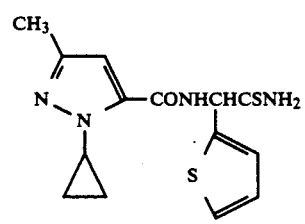

(36) No. 1155
1-cyclopropyl-3-methyl-N-[3-thienyl-(thiocarbamoyl)methyl]-1H-pyrazole-5-carboxamide

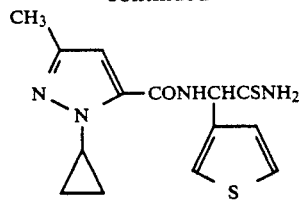

The method for preparation of the compounds of the present invention will be explained hereinafter, by reference to the following reaction scheme I.

Reaction Scheme I: Method for Synthesis of Intermediate

Method 1

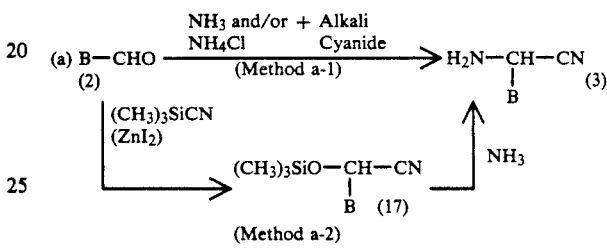

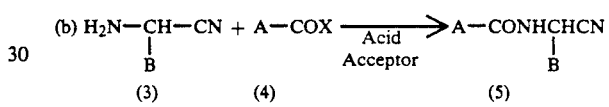

Method 2

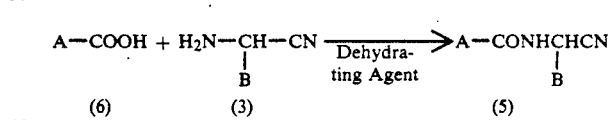

Method 3: Method for Synthesis of Object

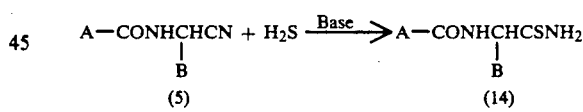

In the said formulae, A and B have the same meaning as mentioned above, and X represents a halogen atom.

Method 1

The aminoacetonitrile derivative (3), which is an intermediate in the first step, can be produced by two ways.

The method (a-1) is one way to produce the derivative (3) by Strecker reaction, where the aldehyde (2), as a starting material, and aqueous ammonia and/or ammonium chloride and an alkali cyanide, such as sodium cyanide, potassium cyanide, etc., are reacted in a binary solvent system comprising an ether, such as ethyl ether, tetrahydrofuran, etc., or an aromatic hydrocarbon, such as benzene, toluene, etc., and water. The reaction temperature is generally preferably from 0° to 100° C. or so.

The method (a-2) is another way to produce the aminoacetonitrile derivative (3), where the aldehyde (2), as a starting material, is reacted with a trialkylsilylnitrile, such as trimethylsilylnitrile, etc., optionally in the presence of a catalytic amount of a Lewis acid, such as zinc iodide, etc., to obtain the intermediate (17), and successively, this intermediate (17) is reacted with an ammonia as dissolved in a solvent, such as methanol, ethanol, etc., to obtain the derivative (3).

The thus-obtained aminoacetonitrile derivative (3) can be purified and isolated by forming a salt with a hydrogen halide, such as hydrogen chloride, etc., in an ether solvent, such as diethyl ether, etc.

Next, in the second step, the aminoacetonitrile derivative (3) as obtained in the first step is reacted with the acid halide having the general formula (4) in the presence of an acid acceptor.

As the acid acceptor, there may be mentioned, for example, organic bases, such as triethylamine, dimethylaniline, pyridine, etc., and inorganic bases, such as ammonia, potassium carbonate, sodium carbonate, ammonium hydrogencarbonate, sodium hydroxide, ammonium carbonate, etc.

The reaction is preferably carried out in the presence of a solvent, for which can be used, for example, ethers, such as diethyl ether, tetrahydrofuran, diisopropyl ether, etc., esters, such as methyl acetate, ethyl acetate, etc., halogenated hydrocarbons, such as methylene chloride, chloroform, 1,2-dichloroethane, etc., acetonitrile and the like. Regarding the reaction temperature, the reaction is desirably carried out under cooling, since this is exothermic, and the reaction temperature is preferably from about −20° to 30° C. or so. Thus, the intended substituted-amido acetonitrile derivatives can be obtained.

Method 2

The starting material carboxylic acid derivative (6) is reacted with the aminoacetonitrile derivative (3) as obtained in the Method 1, in the presence of a dehydrating agent, for dehydrative condensation, to give the intended amido-substituted acetonitrile derivatives.

As the dehydrating agent, carbodiimides, such as dicyclohexylcarbodiimide (DCC), 1-ethyl-3-(3-dimethylaminopropyl)-carbodiimide, etc., as well as inorganic dehydrating agents, such as silicon tetrachloride, etc., are especially preferred.

Method 3

The substituted-amido acetonitrile derivative (5) as obtained in Method 1 or Method 2 is reacted with hydrogen sulfide in the presence of a tertiary amine, such as triethylamine, pyridine, etc., to obtain the intended thioamide derivative (14).

Reaction Scheme II: Synthesis of Intermediate

Method 4

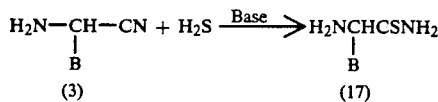

Method 5

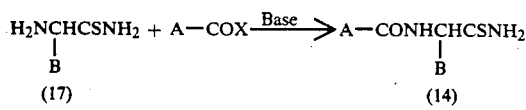

In the above formulae, A, B and X have the same meanings as mentioned above.

Method 6

This method can be carried out under the same reaction condition as that in Method 3.

Method 7

This method can be carried out under the same reaction condition as that in Method 1(b).

The thus-obtained amide derivative can be purified by means of a conventional purification method, for example, including recrystallization, column chromatography or the like, to obtain a pure product.

Concrete examples are described hereinafter to illustrate the method for preparation of the compounds of the present invention, which, however, are not intended to limit the scope of the present invention.

EXAMPLE 1

Production of Compound No. 27

Synthesis of Intermediate

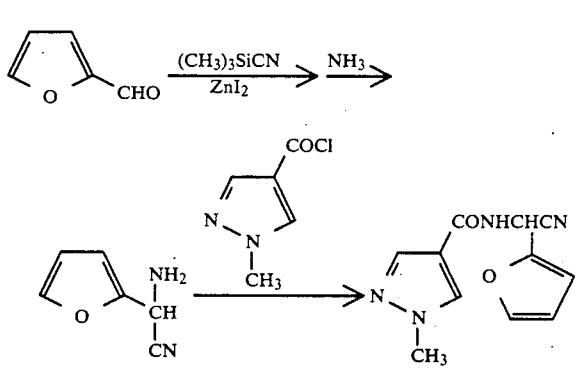

A catalytic amount (50 mg) of zinc iodide was added to furfural (10 g) and trimethylsilyl cyanide (11 g) under cooling with ice and then stirred for 1 hour at room temperature. Afterwards, ammonia-saturated methanol (80 ml) was added thereto and stirred for 2 hours at 40° C. The reaction mixture was concentrated and extracted with ethyl acetate, and then dried, and thereafter the solvent was evaporated out to obtain α-(2-furyl)aminoacetonitrile (11.6 g).

To a THF solution containing the α-(2-furyl)aminoacetonitrile (2.15 g) and triethylamine (1.75 g) was added 1-methyl-1H-pyrazole-4-carboxylic acid chloride (2.55 g) under cooling with ice, and the whole was stirred for 1 hour as such and then for 16 hours at room temperature. The solid product formed was taken out by filtration, and the solvent was evaporated out, and then the thus-obtained oily product was purified by column chromatography and then washed with isopropyl ether, to give 2.55 g of the intended N-(cyano-2-furanylmethyl)-1-methyl-1H-pyrazole-4-carboxamide crystal.

m.p. 160° to 162° C.

$^1$H-NMR: (Solvent CDCl$_3$.DMSO-d$_6$) δ (ppm)=9.16(d,1H, J=7.2 Hz), 8.07(s,1H), 7.84(S,1H), 7.50(m,1H), 6.3 to 6.6(m,2H), 6.31(d,1H,J=7.2 Hz), 3.84(s,3H).

Synthesis of Object

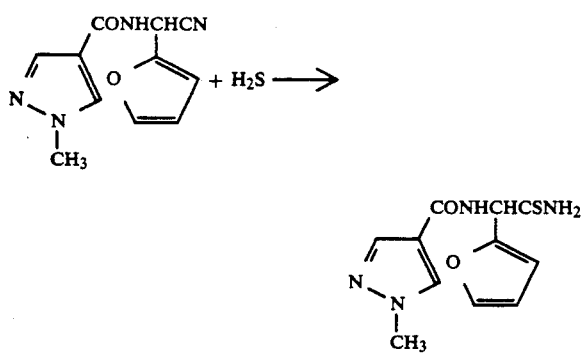

Hydrogen sulfide was blown into an ethanol solution containing 1.4 g of the N-(cyano-2-furanylmethyl)-1-methyl-1H-pyrazol-4-carboxamide as obtained in the above process and 0.7 g of triethylamine, for 1 hour, and the whole was stirred for 1 hour under cooling with ice and then for a further 2 hours at room temperature. Afterwards, the crystal formed was taken out by filtration, washed with chloroform and then dried, to obtain 1.1 g of the intended N-[2-furanyl(thiocarbamoyl)-methyl]-1-methyl-1H-pyrazole-4-carboxamide.

m.p. 203° to 205° C.

$^1$H-NMR: (Solvent CDCl$_3$.DMSO-d$_6$) δ (ppm)=9.79(bs,1H), 9.38(bs,1H), 8.25(d,1H,J=9 Hz), 8.17(s,1H), 7.87(s,1H), 7.46(s,1H), 7.46(m,1H), 6.2 to 6.6(m,2H), 6.04(d,1H,J=9 Hz), 3.83(s,3H).

EXAMPLE 2

Production of Compound No. 1092

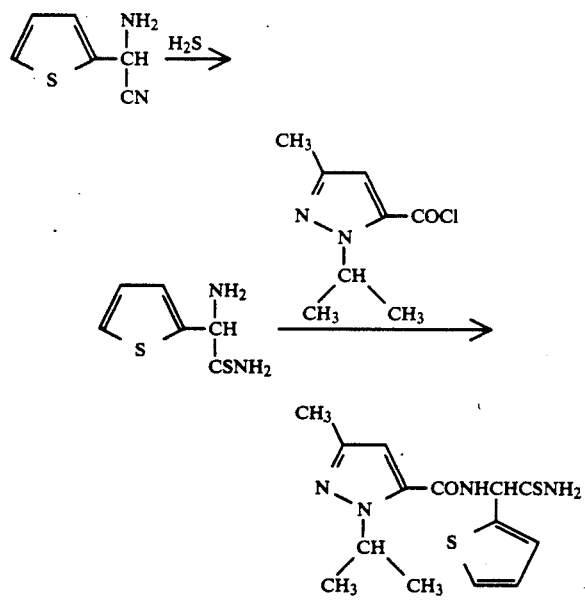

13.8 g (0.1 mol) of α-(2-thienyl)aminoacetonitrile, 10.1 g (0.1 mol) of triethylamine and 10 ml of pyridine were dissolved in 100 ml of toluene. With stirring, 5.1 g (0.15 mol) of hydrogen sulfide gas were introduced into the solution under cooling with ice. When the reaction mixture was stirred overnight at room temperature, a crystal deposition was formed. Subsequently, the solution was concentrated as such, and the obtained crystal was recrystallized from mixed solvent of toluene and ethyl acetate, and then dried, to obtain 11.0 g of the crystals.

It was confirmed by mass spectrographic analysis and $^1$H-NMR that the crystal was the intended α-(2-thienyl)aminoacetothioamide with m.p. 95° to 97°.

3.44 g (0.02 mol) of the α-(2-thienyl)aminoacetothioamide was dissolved in 50 ml of tetrahydrofuran (THF) and successively, 2.4 g (0.024 mol) of triethylamine were added thereto. With stirring of the mixed solution, a solution of 3.72 g (0.02 mol) of 1-isopropyl-3-methyl-pyrazole-5-carboxylic acid chloride in 6.2 ml of tetrahydrofuran (THF) was added thereto dropwise under cooling with ice. Afterwards, it was stirred for 5 hours at room temperature, and the reaction was completed. The reaction mixture was concentrated and the residue was washed with water. The obtained crystal was recrystallized from toluene-ethyl acetate, to obtain 5.35 g of the crystals (according to liquid chromatography, the purity of the crystal was 99%).

The crystal was proved to be the intended 1-isopropyl-3-methyl-N-[2-thienyl(thiocarbamoyl)methyl]-1H-pyrazole-5-carboxamide by mass spectrographic analysis and $^1$H-NMR.

TABLE 1

| | A—CONHCH—D | | | | | | | |
| | | | | B | | | | |
| Compound No. | A | $R_1$ | $R_2$ | $R_3$ | B | $R_4$ | $R_5$ | $R_6$ | D |
|---|---|---|---|---|---|---|---|---|---|
| 27 | A-2 | CH$_3$ | H | H | B-4 | H | H | H | CSNH$_2$ |
| 36 | A-2 | CH$_3$ | H | H | B-5 | H | H | H | CSNH$_2$ |
| 54 | A-3 | CH$_3$ | H | H | B-4 | H | H | H | CSNH$_2$ |
| 56 | A-3 | CH$_3$ | H | H | B-5 | H | H | H | CSNH$_2$ |
| 81 | A-3 | CH$_3$ | CH$_3$ | H | B-4 | H | H | H | CSNH$_2$ |
| 92 | A-3 | CH$_3$ | CH$_3$ | H | B-5 | H | H | H | CSNH$_2$ |
| 121 | A-3 | CH$_3$ | CF$_3$ | H | B-4 | H | H | H | CSNH$_2$ |
| 123 | A-3 | CH$_3$ | CF$_3$ | H | B-5 | H | H | H | CSNH$_2$ |

TABLE 2

| | A—CONHCH—D | | | | | | | |
| | | | | B | | | | |
| Compound No. | A | $R_1$ | $R_2$ | $R_3$ | B | $R_4$ | $R_5$ | $R_6$ | D |
|---|---|---|---|---|---|---|---|---|---|
| 737 | A-2 | CH$_3$ | H | H | B-6 | H | H | H | CSNH$_2$ |
| 739 | A-2 | CH$_3$ | H | H | B-7 | H | H | H | CSNH$_2$ |
| 763 | A-3 | CH$_3$ | CH$_3$ | H | B-6 | H | H | H | CSNH$_2$ |

TABLE 2-continued

A—CONHCH—D
|
B

| Compound No. | A | R₁ | R₂ | R₃ | B | R₄ | R₅ | R₆ | D |
|---|---|---|---|---|---|---|---|---|---|
| 766 | A-3 | $CH_3$ | $CH_3$ | H | B-7 | H | H | H | $CSNH_2$ |
| 789 | A-3 | $CH_3$ | $CF_3$ | H | B-6 | H | H | H | $CSNH_2$ |
| 791 | A-3 | $CH_3$ | $CF_3$ | H | B-7 | H | H | H | $CSNH_2$ |
| 824 | A-3 | $CH_2CH_3$ | $CH_3$ | H | B-6 | H | H | H | $CSNH_2$ |
| 825 | A-3 | $CH_2CH_3$ | $CH_3$ | H | B-7 | H | H | H | $CSNH_2$ |

TABLE 3

A—CONHCH—CSNH₂
|
B

| Compound No. | A | R₁ | R₂ | R₃ | B | R₄ | R₅ | R₆ |
|---|---|---|---|---|---|---|---|---|
| 1075 | A-2 | $CH_3$ | H | H | B-6 | H | H | H |
| 1076 | A-2 | $CH_3$ | $CH_3$ | H | B-4 | H | H | H |
| 1077 | A-2 | $CH_3$ | $CH_3$ | H | B-6 | H | H | H |
| 1078 | A-3 | $CH_3$ | H | H | B-4 | H | H | H |
| 1079 | A-3 | $CH_3$ | H | H | B-5 | H | H | H |
| 1080 | A-3 | $CH_3$ | H | H | B-6 | H | H | H |
| 1081 | A-3 | $C_2H_5$ | H | H | B-4 | H | H | H |
| 1082 | A-3 | $C_2H_5$ | H | H | B-5 | H | H | H |
| 1083 | A-3 | $C_2H_5$ | H | H | B-6 | H | H | H |
| 1084 | A-3 | $C_2H_5$ | H | H | B-7 | H | H | H |
| 1085 | A-3 | $C_2H_5$ | $CH_3$ | H | B-4 | H | H | H |
| 1086 | A-3 | $C_2H_5$ | $CH_3$ | H | B-5 | H | H | H |
| 1087 | A-3 | $C_3H_7$-n | $CH_3$ | H | B-4 | H | H | H |
| 1088 | A-3 | $C_3H_7$-n | $CH_3$ | H | B-5 | H | H | H |
| 1089 | A-3 | $C_3H_7$-n | $CH_3$ | H | B-6 | H | H | H |
| 1090 | A-3 | $C_3H_7$-n | $CH_3$ | H | B-7 | H | H | H |
| 1091 | A-3 | $C_3H_7$-i | $CH_3$ | H | B-4 | H | H | H |
| 1092 | A-3 | $C_3H_7$-i | $CH_3$ | H | B-5 | H | H | H |
| 1093 | A-3 | $C_3H_7$-i | $CH_3$ | H | B-6 | H | H | H |
| 1094 | A-3 | $C_3H_7$-i | $CH_3$ | H | B-7 | H | H | H |
| 1095 | A-3 | $C_3H_7$-i | H | H | B-4 | H | H | H |
| 1096 | A-3 | $C_3H_7$-i | H | H | B-5 | H | H | H |
| 1097 | A-3 | $C_3H_7$-i | H | H | B-6 | H | H | H |
| 1098 | A-3 | $C_3H_7$-i | H | H | B-7 | H | H | H |
| 1099 | A-3 | $C_4H_9$-s | $CH_3$ | H | B-5 | H | H | H |
| 1100 | A-3 | $C_4H_9$-i | $CH_3$ | H | B-5 | H | H | H |
| 1101 | A-3 | $CH(C_2H_5)_2$ | $CH_3$ | H | B-5 | H | H | H |
| 1102 | A-3 | $CH_2CH(CH_3)C_2H_5$ | $CH_3$ | H | B-5 | H | H | H |
| 1103 | A-3 | $CH(CH_3)C_3H_7$-i | $CH_3$ | H | B-5 | H | H | H |
| 1104 | A-3 | $CH(CH_3)CH(CH_3)C_2H_5$ | $CH_3$ | H | B-5 | H | H | H |
| 1105 | A-3 | $CH(C_2H_5)C_3H_7$-i | $CH_3$ | H | B-5 | H | H | H |
| 1106 | A-3 | $CH_2CH_2C_3H_7$-i | $CH_3$ | H | B-5 | H | H | H |
| 1107 | A-3 | $C(CH_3)=CH_2$ | $CH_3$ | H | B-5 | H | H | H |
| 1108 | A-3 | $CH(CH_3CH=CH_2$ | $CH_3$ | H | B-5 | H | H | H |
| 1109 | A-3 | $C(CH_3)=CHCH_3$ | $CH_3$ | H | B-5 | H | H | H |
| 1110 | A-3 | $CH_2C(CH_3)=CH_2$ | $CH_3$ | H | B-5 | H | H | H |
| 1111 | A-3 | $CH(CH_3)C(CH_3)=CH_2$ | $CH_3$ | H | B-5 | H | H | H |
| 1112 | A-3 | $C(C_2H_5)=CH_2$ | $CH_3$ | H | B-5 | H | H | H |
| 1113 | A-3 | $CH=C(CH_3)_2$ | $CH_3$ | H | B-5 | H | H | H |
| 1114 | A-3 | $C(CH_3)=C(CH_3)_2$ | $CH_3$ | H | B-5 | H | H | H |
| 1115 | A-3 | $CH_2C(CH_3)=CHCH_3$ | $CH_3$ | H | B-5 | H | H | H |
| 1116 | A-3 | $CH_2CH=C(CH_3)_2$ | $CH_3$ | H | B-5 | H | H | H |
| 1117 | A-3 | $C_3H_5$-cyclo | $CH_3$ | H | B-5 | H | H | H |
| 1118 | A-3 | $C_4H_7$-cyclo | $CH_3$ | H | B-5 | H | H | H |
| 1119 | A-3 | $C_5H_9$-cyclo | $CH_3$ | H | B-5 | H | H | H |
| 1120 | A-3 | $C_6H_{11}$-cyclo | $CH_3$ | H | B-5 | H | H | H |
| 1121 | A-3 | A-19 | $CH_3$ | H | B-5 | H | H | H |
| 1122 | A-3 | A-20 | $CH_3$ | H | B-4 | H | H | H |
| 1123 | A-3 | A-20 | $CH_3$ | H | B-5 | H | H | H |
| 1124 | A-3 | A-20 | $CH_3$ | H | B-6 | H | H | H |
| 1125 | A-3 | A-20 | $CH_3$ | H | B-7 | H | H | H |
| 1126 | A-3 | A-21 | $CH_3$ | H | B-5 | H | H | H |
| 1127 | A-3 | A-22 | $CH_3$ | H | B-5 | H | H | H |
| 1128 | A-3 | A-23 | $CH_3$ | H | B-5 | H | H | H |
| 1129 | A-3 | A-24 | $CH_3$ | H | B-5 | H | H | H |
| 1130 | A-3 | A-25 | $CH_3$ | H | B-5 | H | H | H |
| 1131 | A-3 | $CHFCH_3$ | $CH_3$ | H | B-5 | H | H | H |
| 1132 | A-3 | $CHClCH_3$ | $CH_3$ | H | B-5 | H | H | H |
| 1133 | A-3 | $CHClCH_2CH_3$ | $CH_3$ | H | B-5 | H | H | H |
| 1134 | A-3 | $CH(CH_3)CH_2F$ | $CH_3$ | H | B-5 | H | H | H |

TABLE 3-continued $$A-CONHCH-CSNH_2$$
$$|$$
$$B$$

| Compound No. | A | $R_1$ | $R_2$ | $R_3$ | B | $R_4$ | $R_5$ | $R_6$ |
|---|---|---|---|---|---|---|---|---|
| 1135 | A-3 | $CH(CH_3)CH_2Cl$ | $CH_3$ | H | B-5 | H | H | H |
| 1136 | A-3 | $CH_2CHFCH_3$ | $CH_3$ | H | B-5 | H | H | H |
| 1137 | A-3 | $CH_2CHClCH_3$ | $CH_3$ | H | B-5 | H | H | H |
| 1138 | A-3 | $CHClCH(CH_3)_2$ | $CH_3$ | H | B-5 | H | H | H |
| 1139 | A-3 | $CH(CH_3)CHClCH_3$ | $CH_3$ | H | B-5 | H | H | H |
| 1140 | A-3 | $CH_2CHClC_2H_5$ | $CH_3$ | H | B-5 | H | H | H |
| 1141 | A-3 | $CH_2CH(CH_3)CH_2Cl$ | $CH_3$ | H | B-5 | H | H | H |
| 1142 | A-3 | $CH_2CH_2OCH_3$ | $CH_3$ | H | B-5 | H | H | H |
| 1143 | A-3 | $CH_2CH(CH_3)OCH_3$ | $CH_3$ | H | B-5 | H | H | H |
| 1144 | A-3 | $CH(CH_3)CH(CH_3)OCH_3$ | $CH_3$ | H | B-5 | H | H | H |
| 1145 | A-3 | $CH=CHCH_3$ | $CH_3$ | H | B-5 | H | H | H |
| 1146 | A-3 | $CH_2-CH=CHCH_3$ | $CH_3$ | H | B-5 | H | H | H |
| 1147 | A-3 | $CH_2C-CH$ | $CH_3$ | H | B-5 | H | H | H |
| 1148 | A-3 | $CH(CH_3)C-CH$ | $CH_3$ | H | B-5 | H | H | H |
| 1149 | A-3 | $CH_2C-CHCH_3$ | $CH_3$ | H | B-5 | H | H | H |
| 1150 | A-3 | $CH(C_2H_5)C-CH$ | $CH_3$ | H | B-5 | H | H | H |
| 1151 | A-3 | $CH_2C-CCH_3$ | $CH_3$ | H | B-5 | H | H | H |
| 1152 | A-3 | $CH_2CH_2C-CH$ | $CH_3$ | H | B-5 | H | H | H |
| 1153 | A-3 | $C_3H_5cyclo$ | $CH_3$ | H | B-4 | H | H | H |
| 1154 | A-3 | $C_3H_5cyclo$ | $CH_3$ | H | B-6 | H | H | H |
| 1155 | A-3 | $C_3H_5cyclo$ | $CH_3$ | H | B-7 | H | H | H |
| 1156 | A-3 | $C_4H_7cyclo$ | $CH_3$ | H | B-4 | H | H | H |
| 1157 | A-3 | $C_4H_7cyclo$ | $CH_3$ | H | B-6 | H | H | H |
| 1158 | A-3 | $C_4H_7cyclo$ | $CH_3$ | H | B-7 | H | H | H |
| 1159 | A-3 | $C_5H_9cyclo$ | $CH_3$ | H | B-4 | H | H | H |
| 1160 | A-3 | $C_5H_9cyclo$ | $CH_3$ | H | B-6 | H | H | H |
| 1161 | A-3 | $C_5H_9cyclo$ | $CH_3$ | H | B-7 | H | H | H |
| 1162 | A-3 | $C_6H_{11}cyclo$ | $CH_3$ | H | B-4 | H | H | H |
| 1163 | A-3 | $C_6H_{11}cyclo$ | $CH_3$ | H | B-6 | H | H | H |
| 1164 | A-3 | $C_6H_{11}cyclo$ | $CH_3$ | H | B-7 | H | H | H |
| 1165 | A-3 | $C_7H_{13}cyclo$ | $CH_3$ | H | B-4 | H | H | H |
| 1166 | A-3 | $C_7H_{13}cyclo$ | H | H | B-5 | H | H | H |
| 1167 | A-3 | $C_7H_{13}cyclo$ | $CH_3$ | H | B-6 | H | H | H |
| 1168 | A-3 | $C_7H_{13}cyclo$ | $CH_3$ | H | B-7 | H | H | H |
| 1169 | A-3 | $C_8H_{15}cyclo$ | $CH_3$ | H | B-4 | H | H | H |
| 1170 | A-3 | $C_8H_{15}cyclo$ | $CH_3$ | H | B-5 | H | H | H |
| 1171 | A-3 | $C_8H_{15}cyclo$ | $CH_3$ | H | B-6 | H | H | H |
| 1172 | A-3 | $C_8H_{15}cyclo$ | $CH_3$ | H | B-7 | H | H | H |
| 1173 | A-3 | A26 | $CH_3$ | H | B-4 | H | H | H |
| 1174 | A-3 | A26 | $CH_3$ | H | B-5 | H | H | H |
| 1175 | A-3 | A26 | $CH_3$ | H | B-6 | H | H | H |
| 1176 | A-3 | A26 | $CH_3$ | H | B-7 | H | H | H |
| 1177 | A-3 | A27 | $CH_3$ | H | B-4 | H | H | H |
| 1178 | A-3 | A27 | $CH_3$ | H | B-5 | H | H | H |
| 1179 | A-3 | A27 | $CH_3$ | H | B-6 | H | H | H |
| 1180 | A-3 | A27 | $CH_3$ | H | B-7 | H | H | H |
| 1181 | A-3 | A28 | $CH_3$ | H | B-4 | H | H | H |
| 1182 | A-3 | A28 | $CH_3$ | H | B-5 | H | H | H |
| 1183 | A-3 | A28 | $CH_3$ | H | B-6 | H | H | H |
| 1184 | A-3 | A28 | $CH_3$ | H | B-7 | H | H | H |
| 1185 | A-3 | A29 | $CH_3$ | H | B-4 | H | H | H |
| 1186 | A-3 | A29 | $CH_3$ | H | B-5 | H | H | H |
| 1187 | A-3 | A29 | $CH_3$ | H | B-6 | H | H | H |
| 1188 | A-3 | A29 | $CH_3$ | H | B-7 | H | H | H |
| 1189 | A-3 | A30 | $CH_3$ | H | B-4 | H | H | H |
| 1190 | A-3 | A30 | $CH_3$ | H | B-5 | H | H | H |
| 1191 | A-3 | A30 | $CH_3$ | H | B-6 | H | H | H |
| 1192 | A-3 | A30 | $CH_3$ | H | B-7 | H | H | H |
| 1193 | A-3 | A31 | $CH_3$ | H | B-4 | H | H | H |
| 1194 | A-3 | A31 | $CH_3$ | H | B-5 | H | H | H |
| 1195 | A-3 | A31 | $CH_3$ | H | B-6 | H | H | H |
| 1196 | A-3 | A31 | $CH_3$ | H | B-7 | H | H | H |
| 1197 | A-3 | A32 | $CH_3$ | H | B-4 | H | H | H |
| 1198 | A-3 | A32 | $CH_3$ | H | B-5 | H | H | H |
| 1199 | A-3 | A32 | $CH_3$ | H | B-6 | H | H | H |
| 1200 | A-3 | A32 | $CH_3$ | H | B-7 | H | H | H |
| 1201 | A-3 | A33 | $CH_3$ | H | B-4 | H | H | H |
| 1202 | A-3 | A33 | $CH_3$ | H | B-5 | H | H | H |
| 1203 | A-3 | A33 | $CH_3$ | H | B-6 | H | H | H |
| 1204 | A-3 | A33 | $CH_3$ | H | B-7 | H | H | H |
| 1205 | A-3 | A34 | $CH_3$ | H | B-4 | H | H | H |
| 1206 | A-3 | A34 | $CH_3$ | H | B-5 | H | H | H |
| 1207 | A-3 | A34 | $CH_3$ | H | B-6 | H | H | H |
| 1208 | A-3 | A34 | $CH_3$ | H | B-7 | H | H | H |
| 1209 | A-3 | A35 | $CH_3$ | H | B-4 | H | H | H |
| 1210 | A-3 | A35 | $CH_3$ | H | B-5 | H | H | H |

TABLE 3-continued

A—CONHCH—CSNH$_2$
         |
         B

| Compound No. | A | R$_1$ | R$_2$ | R$_3$ | B | R$_4$ | R$_5$ | R$_6$ |
|---|---|---|---|---|---|---|---|---|
| 1211 | A-3 | A35 | CH$_3$ | H | B-6 | H | H | H |
| 1212 | A-3 | A35 | CH$_3$ | H | B-7 | H | H | H |
| 1213 | A-3 | A36 | CH$_3$ | H | B-4 | H | H | H |
| 1214 | A-3 | A36 | CH$_3$ | H | B-5 | H | H | H |
| 1215 | A-3 | A36 | CH$_3$ | H | B-6 | H | H | H |
| 1216 | A-3 | A36 | CH$_3$ | H | B-7 | H | H | H |
| 1217 | A-3 | A37 | CH$_3$ | H | B-4 | H | H | H |
| 1218 | A-3 | A37 | CH$_3$ | H | B-5 | H | H | H |
| 1219 | A-3 | A37 | CH$_3$ | H | B-6 | H | H | H |
| 1220 | A-3 | A37 | CH$_3$ | H | B-7 | H | H | H |
| 1221 | A-3 | A38 | CH$_3$ | H | B-4 | H | H | H |
| 1222 | A-3 | A38 | CH$_3$ | H | B-5 | H | H | H |
| 1223 | A-3 | A38 | CH$_3$ | H | B-6 | H | H | H |
| 1224 | A-3 | A38 | CH$_3$ | H | B-7 | H | H | H |
| 1225 | A-3 | A39 | CH$_3$ | H | B-4 | H | H | H |
| 1226 | A-3 | A39 | CH$_3$ | H | B-5 | H | H | H |
| 1227 | A-3 | A39 | CH$_3$ | H | B-6 | H | H | H |
| 1228 | A-3 | A39 | CH$_3$ | H | B-7 | H | H | H |
| 1229 | A-3 | A40 | CH$_3$ | H | B-4 | H | H | H |
| 1230 | A-3 | A40 | CH$_3$ | H | B-5 | H | H | H |
| 1231 | A-3 | A40 | CH$_3$ | H | B-6 | H | H | H |
| 1232 | A-3 | A40 | CH$_3$ | H | B-7 | H | H | H |
| 1233 | A-3 | A41 | CH$_3$ | H | B-4 | H | H | H |
| 1234 | A-3 | A41 | CH$_3$ | H | B-5 | H | H | H |
| 1235 | A-3 | A41 | CH$_3$ | H | B-6 | H | H | H |
| 1236 | A-3 | A41 | CH$_3$ | H | B-7 | H | H | H |
| 1237 | A-3 | A42 | CH$_3$ | H | B-4 | H | H | H |
| 1238 | A-3 | A42 | CH$_3$ | H | B-5 | H | H | H |
| 1239 | A-3 | A42 | CH$_3$ | H | B-6 | H | H | H |
| 1240 | A-3 | A42 | CH$_3$ | H | B-7 | H | H | H |
| 1241 | A-3 | A43 | CH$_3$ | H | B-4 | H | H | H |
| 1242 | A-3 | A43 | CH$_3$ | H | B-5 | H | H | H |
| 1243 | A-3 | A43 | CH$_3$ | H | B-6 | H | H | H |
| 1244 | A-3 | A43 | CH$_3$ | H | B-7 | H | H | H |
| 1245 | A-3 | A44 | CH$_3$ | H | B-4 | H | H | H |
| 1246 | A-3 | A44 | CH$_3$ | H | B-5 | H | H | H |
| 1247 | A-3 | A44 | CH$_3$ | H | B-6 | H | H | H |
| 1248 | A-3 | A44 | CH$_3$ | H | B-7 | H | H | H |
| 1249 | A-3 | A45 | CH$_3$ | H | B-4 | H | H | H |
| 1250 | A-3 | A45 | CH$_3$ | H | B-5 | H | H | H |
| 1251 | A-3 | A45 | CH$_3$ | H | B-6 | H | H | H |
| 1252 | A-3 | A45 | CH$_3$ | H | B-7 | H | H | H |
| 1253 | A-3 | A46 | CH$_3$ | H | B-4 | H | H | H |
| 1254 | A-3 | A46 | CH$_3$ | H | B-5 | H | H | H |
| 1255 | A-3 | A46 | CH$_3$ | H | B-6 | H | H | H |
| 1256 | A-3 | A46 | CH$_3$ | H | B-7 | H | H | H |
| 1257 | A-3 | A47 | CH$_3$ | H | B-4 | H | H | H |
| 1290 | A-3 | A47 | CH$_3$ | H | B-5 | H | H | H |
| 1291 | A-3 | A47 | CH$_3$ | H | B-6 | H | H | H |
| 1292 | A-3 | A47 | CH$_3$ | H | B-7 | H | H | H |
| 1293 | A-3 | A48 | CH$_3$ | H | B-4 | H | H | H |
| 1294 | A-3 | A48 | CH$_3$ | H | B-5 | H | H | H |
| 1295 | A-3 | A48 | CH$_3$ | H | B-6 | H | H | H |
| 1296 | A-3 | A48 | CH$_3$ | H | B-7 | H | H | H |
| 1297 | A-3 | A49 | CH$_3$ | H | B-4 | H | H | H |
| 1298 | A-3 | A49 | CH$_3$ | H | B-5 | H | H | H |
| 1299 | A-3 | A49 | CH$_3$ | H | B-6 | H | H | H |
| 1300 | A-3 | A49 | CH$_3$ | H | B-7 | H | H | H |
| 1301 | A-3 | A50 | CH$_3$ | H | B-4 | H | H | H |
| 1302 | A-3 | A50 | CH$_3$ | H | B-5 | H | H | H |
| 1303 | A-3 | A50 | CH$_3$ | H | B-6 | H | H | H |
| 1304 | A-3 | A50 | CH$_3$ | H | B-7 | H | H | H |
| 1305 | A-3 | A51 | CH$_3$ | H | B-4 | H | H | H |
| 1306 | A-3 | A51 | CH$_3$ | H | B-5 | H | H | H |
| 1307 | A-3 | A51 | CH$_3$ | H | B-6 | H | H | H |
| 1308 | A-3 | A51 | CH$_3$ | H | B-7 | H | H | H |
| 1309 | A-3 | A52 | CH$_3$ | H | B-4 | H | H | H |
| 1310 | A-3 | A52 | CH$_3$ | H | B-5 | H | H | H |
| 1311 | A-3 | A52 | CH$_3$ | H | B-6 | H | H | H |
| 1312 | A-3 | A52 | CH$_3$ | H | B-7 | H | H | H |
| 1313 | A-3 | A53 | CH$_3$ | H | B-4 | H | H | H |
| 1314 | A-3 | A53 | CH$_3$ | H | B-5 | H | H | H |
| 1315 | A-3 | A53 | CH$_3$ | H | B-6 | H | H | H |
| 1316 | A-3 | A53 | CH$_3$ | H | B-7 | H | H | H |
| 1317 | A-3 | A54 | CH$_3$ | H | B-4 | H | H | H |
| 1318 | A-3 | A54 | CH$_3$ | H | B-5 | H | H | H |

TABLE 3-continued

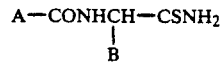

| Compound No. | A | $R_1$ | $R_2$ | $R_3$ | B | $R_4$ | $R_5$ | $R_6$ |
|---|---|---|---|---|---|---|---|---|
| 1319 | A-3 | A54 | $CH_3$ | H | B-6 | H | H | H |
| 1320 | A-3 | A54 | $CH_3$ | H | B-7 | H | H | H |
| 1321 | A-3 | A55 | $CH_3$ | H | B-4 | H | H | H |
| 1322 | A-3 | A55 | $CH_3$ | H | B-5 | H | H | H |
| 1323 | A-3 | A55 | $CH_3$ | H | B-6 | H | H | H |
| 1324 | A-3 | A55 | $CH_3$ | H | B-7 | H | H | H |
| 1325 | A-3 | A56 | $CH_3$ | H | B-4 | H | H | H |
| 1326 | A-3 | A56 | $CH_3$ | H | B-5 | H | H | H |
| 1327 | A-3 | A56 | $CH_3$ | H | B-6 | H | H | H |
| 1328 | A-3 | A56 | $CH_3$ | H | B-7 | H | H | H |
| 1329 | A-3 | A57 | $CH_3$ | H | B-4 | H | H | H |
| 1330 | A-3 | A57 | $CH_3$ | H | B-5 | H | H | H |
| 1331 | A-3 | A57 | $CH_3$ | H | B-6 | H | H | H |
| 1332 | A-3 | A57 | $CH_3$ | H | B-7 | H | H | H |
| 1333 | A-3 | A58 | $CH_3$ | H | B-4 | H | H | H |
| 1334 | A-3 | A58 | $CH_3$ | H | B-5 | H | H | H |
| 1335 | A-3 | A58 | $CH_3$ | H | B-6 | H | H | H |
| 1336 | A-3 | A58 | $CH_3$ | H | B-7 | H | H | H |
| 1337 | A-3 | A59 | $CH_3$ | H | B-4 | H | H | H |
| 1338 | A-3 | A59 | $CH_3$ | H | B-5 | H | H | H |
| 1339 | A-3 | A59 | $CH_3$ | H | B-6 | H | H | H |
| 1340 | A-3 | A59 | $CH_3$ | H | B-7 | H | H | H |
| 1341 | A-3 | A60 | $CH_3$ | H | B-4 | H | H | H |
| 1342 | A-3 | A60 | $CH_3$ | H | B-5 | H | H | H |
| 1343 | A-3 | A60 | $CH_3$ | H | B-6 | H | H | H |
| 1344 | A-3 | A60 | $CH_3$ | H | B-7 | H | H | H |
| 1345 | A-3 | A61 | $CH_3$ | H | B-4 | H | H | H |
| 1346 | A-3 | A61 | $CH_3$ | H | B-5 | H | H | H |
| 1347 | A-3 | A61 | $CH_3$ | H | B-6 | H | H | H |
| 1348 | A-3 | A61 | $CH_3$ | H | B-7 | H | H | H |
| 1349 | A-3 | A62 | $CH_3$ | H | B-4 | H | H | H |
| 1350 | A-3 | A62 | $CH_3$ | H | B-5 | H | H | H |
| 1351 | A-3 | A62 | $CH_3$ | H | B-6 | H | H | H |
| 1352 | A-3 | A62 | $CH_3$ | H | B-7 | H | H | H |
| 1353 | A-3 | A63 | $CH_3$ | H | B-4 | H | H | H |
| 1354 | A-3 | A63 | $CH_3$ | H | B-5 | H | H | H |
| 1355 | A-3 | A63 | $CH_3$ | H | B-6 | H | H | H |
| 1356 | A-3 | A63 | $CH_3$ | H | B-7 | H | H | H |
| 1357 | A-3 | A64 | $CH_3$ | H | B-4 | H | H | H |
| 1358 | A-3 | A64 | $CH_3$ | H | B-5 | H | H | H |
| 1359 | A-3 | A64 | $CH_3$ | H | B-6 | H | H | H |
| 1360 | A-3 | A64 | $CH_3$ | H | B-7 | H | H | H |
| 1361 | A-3 | A65 | $CH_3$ | H | B-4 | H | H | H |
| 1362 | A-3 | A65 | $CH_3$ | H | B-5 | H | H | H |
| 1363 | A-3 | A65 | $CH_3$ | H | B-6 | H | H | H |
| 1364 | A-3 | A65 | $CH_3$ | H | B-7 | H | H | H |
| 1365 | A-3 | A66 | $CH_3$ | H | B-4 | H | H | H |
| 1366 | A-3 | A66 | $CH_3$ | H | B-5 | H | H | H |
| 1367 | A-3 | A66 | $CH_3$ | H | B-6 | H | H | H |
| 1368 | A-3 | A66 | $CH_3$ | H | B-7 | H | H | H |
| 1369 | A-3 | A67 | $CH_3$ | H | B-4 | H | H | H |
| 1370 | A-3 | A67 | $CH_3$ | H | B-5 | H | H | H |
| 1371 | A-3 | A67 | $CH_3$ | H | B-6 | H | H | H |
| 1372 | A-3 | A67 | $CH_3$ | H | B-7 | H | H | H |
| 1373 | A-3 | A68 | $CH_3$ | H | B-4 | H | H | H |
| 1374 | A-3 | A68 | $CH_3$ | H | B-5 | H | H | H |
| 1375 | A-3 | A68 | $CH_3$ | H | B-6 | H | H | H |
| 1376 | A-3 | A68 | $CH_3$ | H | B-7 | H | H | H |
| 1377 | A-3 | A69 | $CH_3$ | H | B-4 | H | H | H |
| 1378 | A-3 | A69 | $CH_3$ | H | B-5 | H | H | H |
| 1379 | A-3 | A69 | $CH_3$ | H | B-6 | H | H | H |
| 1380 | A-3 | A69 | $CH_3$ | H | B-7 | H | H | H |
| 1381 | A-3 | A70 | $CH_3$ | H | B-4 | H | H | H |
| 1382 | A-3 | A70 | $CH_3$ | H | B-5 | H | H | H |
| 1383 | A-3 | A70 | $CH_3$ | H | B-6 | H | H | H |
| 1384 | A-3 | A70 | $CH_3$ | H | B-7 | H | H | H |
| 1385 | A-3 | A71 | $CH_3$ | H | B-4 | H | H | H |
| 1386 | A-3 | A71 | $CH_3$ | H | B-5 | H | H | H |
| 1387 | A-3 | A71 | $CH_3$ | H | B-6 | H | H | H |
| 1388 | A-3 | A71 | $CH_3$ | H | B-7 | H | H | H |
| 1389 | A-3 | A72 | $CH_3$ | H | B-4 | H | H | H |
| 1390 | A-3 | A72 | $CH_3$ | H | B-5 | H | H | H |
| 1391 | A-3 | A72 | $CH_3$ | H | B-6 | H | H | H |
| 1392 | A-3 | A72 | $CH_3$ | H | B-7 | H | H | H |
| 1393 | A-3 | A73 | $CH_3$ | H | B-4 | H | H | H |
| 1394 | A-3 | A73 | $CH_3$ | H | B-5 | H | H | H |

TABLE 3-continued $$A-CONHCH-CSNH_2$$
$$\phantom{A-CONHCH}|$$
$$\phantom{A-CONHCH-C}B$$

| Compound No. | A | $R_1$ | $R_2$ | $R_3$ | B | $R_4$ | $R_5$ | $R_6$ |
|---|---|---|---|---|---|---|---|---|
| 1395 | A-3 | A73 | CH$_3$ | H | B-6 | H | H | H |
| 1398 | A-3 | A73 | CH$_3$ | H | B-7 | H | H | H |
| 1399 | A-3 | A74 | CH$_3$ | H | B-4 | H | H | H |
| 1400 | A-3 | A74 | CH$_3$ | H | B-5 | H | H | H |
| 1401 | A-3 | A74 | CH$_3$ | H | B-6 | H | H | H |
| 1402 | A-3 | A74 | CH$_3$ | H | B-7 | H | H | H |

The groups representing A and B shown in the above-mentioned Tables 1–3 are groups represented by the following formulae.

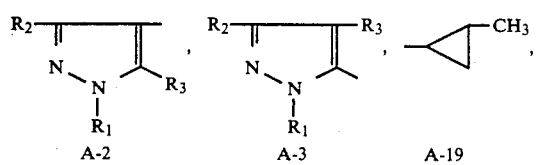

A-2, A-3, A-19

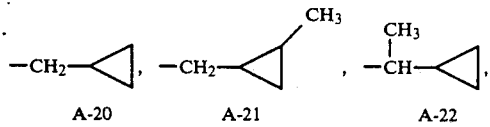

A-20, A-21, A-22

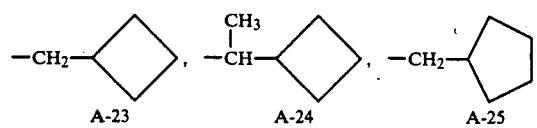

A-23, A-24, A-25

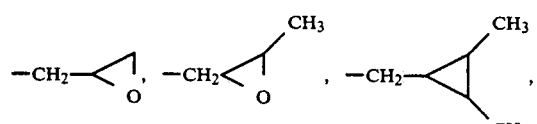

A-26, A-27, A-28

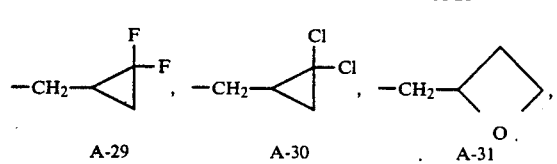

A-29, A-30, A-31

-continued

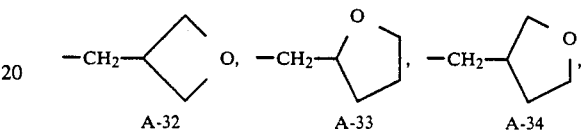

A-32, A-33, A-34

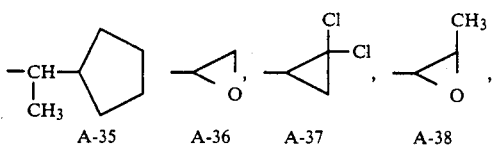

A-35, A-36, A-37, A-38

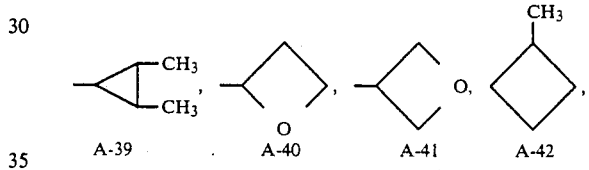

A-39, A-40, A-41, A-42

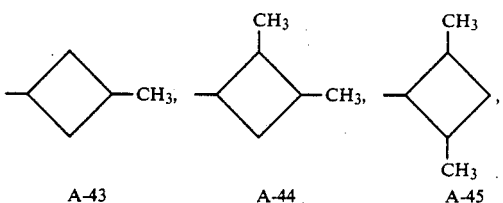

A-43, A-44, A-45

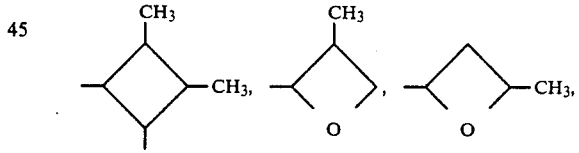

A-46, A-47, A-48

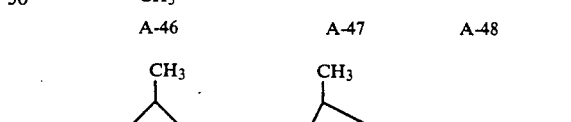

A-49, A-50, A-51

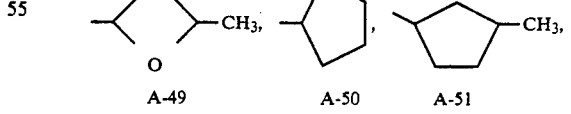

A-52, A-53, A-54

-continued

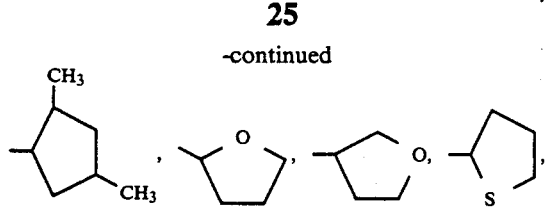

A-55, A-56, A-57, A-58

-continued

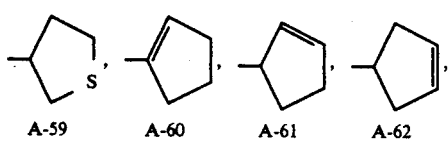

A-73, A-74

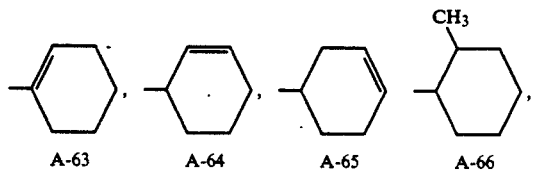

B-4, B-5, B-6, B-7

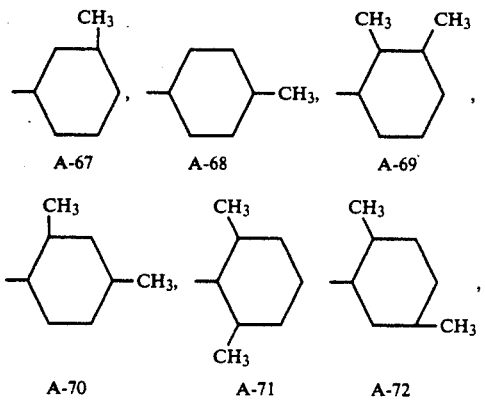

A-59, A-60, A-61, A-62

A-63, A-64, A-65, A-66

A-67, A-68, A-69

A-70, A-71, A-72

The data of H-NMR and the melting points of some compounds described in Tables 1–3 are shown in Table 4.

TABLE 4

| Compound No. | Solvent | ppm (Standard TMS) | M.P. (°C.) |
|---|---|---|---|
| 36 | CDCl$_3$ DMSO d-6 | 3.84(s, 3H), 6.18(d, 1H, J=8.4Hz), 6.80~7.50(m, 3H), 7.87(s, 1H), 8.22(s, 1H), 8.26(d, 1H, J=8.4Hz), 9.55(bs, 1H), 9.87(bs, 1H) | 200~203 |
| 47 | CD$_3$OD | 3.80(s, 3H), 6.00(m, 1H), 6.80(m, 2H), 7.20(m, 2H), 7.67~8.00(m, 2H) | 128~129 |
| 739 | CDCl$_3$ + DMSO d-6 | 3.85(s, 3H), 6.02(d, 1H, J=8.4Hz), 7.05~7.60(m, 3H), 7.85(s, 1H), 8.18(s, 1H), 8.75(d, 1H, J=8.4Hz), 9.44(bs, 1H), 9.71(bs, 1H) | 224~227 |
| 763 | DMSO d-6 | 2.05(s, 3H), 3.83(s, 3H), 5.70(d, 1H, J=7.8Hz), 6.50(s, 1H), 6.57(s, 1H), 7.42~7.71(m, 2H), 8.35(d, 1H, J=7.8Hz), 9.37(bs, 1H), 9.70(bs, 1H) | 41~43 |
| 766 | CDCl$_3$ + DMSO d-6 | 2.23(s, 3H), 4.03(s, 3H), 6.05(d, 1H, J=7.8Hz), 6.51(s, 1H), 7.18~7.53(m, 3H), 8.10(d, 1H, J=7.8Hz), 9.18(s, 2H) | 170~171 |
| 824 | DMSO d-6 | 1.20(t, 3H, J=7.2Hz), 2.10(s, 3H), 4.31(q, 2H, J=7.2Hz), 5.74(d, 1H, J=8.4Hz), 6.52(s, 1H), 6.62(s, 1H), 7.44~7.81(m, 2H), 8.38(d, 1H, J=8.4Hz), 9.38(bs, 1H), 9.70(bs, 1H) | 138~140 |
| 825 | CDCl$_3$ + DMSO d-6 | 1.35(t, 3H, J=7.2Hz), 2.24(s, 3H), 4.45(q, 2H, J=7.2Hz), 6.03(d, 1H, J=7.8Hz), 6.52(s, 1H), 7.08~7.53 (m, 3H), 8.15(d, 1H, J=7.8Hz), | 162~163 |

TABLE 4-continued

| Compound No. | Solvent | ppm (Standard TMS) | M.P. (°C.) |
|---|---|---|---|
| 81 | CDCl₃ + DMSO d-6 | 9.35(s, 2H) 2.20(s, 3H), 4.00(s, 3H), 6.03(d, 1H, J=8.4Hz), 6.40(m, 2H), 6.67(s, 1H), 7.47(brs, 1H), 8.37 (d, 1H, J=8.4Hz), 9.40(brs, 1H), 9.80(brs.1H), | 149~150 |
| 92 | CDCl₃ + DMSO d-6 | 2.17(s, 3H), 3.90(s,3H), 6.16(d, 1H, J=7.8Hz), 6.65(s, 1H), 6.80~7.50(m, 3H), 8.47(d, 1H, J=7.8Hz) 9.59(bs, 1H), 9.91(bs, 1H) | 150~152 |
| 1075 | CDCl₃ + DMSO d-6 | 3.84(s, (3H)) 5.91(d, (1H)J=7.8 Hz) 6.33~6.62(m, (1H)) 7.15~7.38 (m, (1H)) 7.38~7.70(m, (1H)) 7.76 (s, (1H)) 7.95(d, (1H), J=7.8Hz) 7.97 (s, (1H))9.15(brs, (1H)) 9.29(brs, (1H)) | 182~184 (Decomp.) |
| 1076 | CDCl₃ + DMSO d-6 | 2.42(s, (3H)) 3.75(s, (3H)) 6.03(d, (1H)J=8.4Hz) 6.14 6.43 (m, (2H)) 7.18~7.37(m(1H)) 7.64 (d, (1H), J=8.4Hz)7.85(s, (1H)) 9.06 (brs,(1H)) 9.28(brs, (1H)) | 152~154 |
| 1077 | CDCl₃ + DMSO d-6 | 2.40(s, (3H)) 3.73(s, (3H)) 5.89(d, (1H)J=8.0Hz)6.36~6.48(m,(1H)) 7.15~7.36, (1H)) 7.36~7.49(m, (1H)) 7.59(d, (1H), J=8.0Hz) 7.82(s, (1H)) 9.16(brs, (2H)) | 181~184 (Decomp.) |
| 1078 | CDCl₃ + DMSO d-6 | 4.05(s, (3H)) 6.02(d, (1H), J=7.8Hz) 6.16-6.46(m, (2H)) 6.74(d, (1H), J=1.2Hz) 7.12-7.44(m, (2H)) 8.18 (d, (1H), J=7.8Hz) 9.09(brs, (1H)) 9.38(brs, (1H)) | 152~155 |
| 1080 | CDCl₃ + DMSO d-6 | 4.04(s, 3H), 5.86(d, (1H), J=7.8Hz) 6.37-6.59(m, (1H)) 6.72(d, (1H), J=1.8Hz) 7.14-7.41(m, (2H)) 7.41-7.62(m, (1H)) 8.14(d, (1H), J=7.8Hz) 9.17(brs, (1H)) 9.37(brs, (1H)) | 136~139 |
| 1081 | CDCl₃ + DMSO d-6 | 1.36(t, (3H), J=6.6Hz) 4.49(q, (2H), J=6.6Hz) 6.02(d, (1H), J=7.8Hz) 6.71-6.50(m, (2H)) 6.75(d, (1H), J=1.2Hz) 7.20-7.46(m, (2H)) 6.20 (d, (1H), J=7.8Hz) 9.15(brs, (1H)) 9.46(brs, (1H)) | 118~122 |
| 1082 | CDCl₃ + DMSO d-6 | 1.36(t, (3H), J=7.2Hz) 4.50(q, (2H), J=7.2Hz) 6.16(d, (1H), J=8.4Hz) 6.67(d, (1H), J=1.8Hz) 6.7-7.0(m, (1H)) 7.0-7.29(m, (2H)) 7.33(d, (1H), J=1.8Hz) 8.16(d, (1H), J=8.4Hz) 9.27(brs, (2H)) | 147~149 |
| 1083 | CDCl₃ + DMSO d-6 | 1.36(t, (3H), J=7.2Hz) 4.48(q,(2H), J=7.2Hz) 5.86(d, (1H), J=8.1Hz) 6.35-6.57(m, (1H)) 6.67(d, (1H), J=1.8Hz) 7.14-7.42(m, (2H)) 7.42-7.63(m, (1H)) 8.07(d, (1H), J=8.1Hz) 9.12(brs, (1H)) 9.26(brs, (1H)) | 166~168 |
| 1084 | CDCl₃ + DMSO d-6 | 1.36(t, (3H), J=7.2Hz) 4.48(q, (2H), J=7.2Hz) 6.58(d, (1H), J=7.8Hz) 6.70(d, (1H), J=1.8Hz) 6.95-7.57(m, (3H)) 8.21(d, (1H), J=7.8Hz) 9.21 (brs, (1H)) 9.37(brs, (1H)) | 161~163 |
| 1085 | CDCl₃ + DMSO d-6 | 1.36(t, 3H, J=7.2Hz) 2.25(s, 3H) 4.48(q, 2H, J=7.2Hz) 6.08(d, 1H, J=7.8Hz) 6.2~6.5(m, 2H) 6.55(s, 1H) 7.3~7.5(m, 1H) 8.12(d, 1H, J=7.8Hz) 9.25(bs, 1H), 9.45(bs, 1H) | 114~115 |
| 1086 | CDCl₃ + DMSO d-6 | 1.34(t, 3H, J=7.2Hz) 2.25(s, 3H) 4.45(q, 2H, J=7.2Hz) 6.21(d, 1H, J=7.8Hz 6.57(s, 1H) 6.85~7.05(m, 1H) 7.1~7.4(m, 2H) 8.36(d, 1H, J=7.8Hz) 9.56(bs, 1H) 9.83(bs, 1H) | 165~167 |
| 1087 | CDCl₃ + DMSO d-6 | 0.85(t, 3H, J=7.2Hz) 1.83(t, 2H, J=7.2Hz) 2.25(s, 3H) 4.38(t, 2H, J=7.2Hz) 6.08(d, 1H, J=7.8Hz) 6.25~6.50(m, 2H) 6.50(s, 1H) 7.3~7.5(m, 1H) 8.19(d, 1H J=7.8Hz) 9.29(bs 1H) 9.65(bs, 1H) | 164~165 |
| 1088 | CDCl₃ + DMSO | 0.85(t, 3H, J=7.2Hz), 1.86(tq, 2H, J=7.2Hz) 2.24(s, 3H), 4.38(t, 2H, J=7.2Hz) 6.24(d, 1H, J=7.8Hz) | 176~178 |

TABLE 4-continued

| Compound No. | Solvent | ppm (Standard TMS) | M.P. (°C.) |
|---|---|---|---|
| | d-6 | 6.58(s, 1H) 6.8~7.05(m, 1H), 7.1~7.4 (m, 2H) 8.34(d, 1H, J=7.8Hz), 9.55 (bs, 1H) 9.79(bs, 1H) | |
| 1089 | CDCl$_3$ + DMSO d-6 | 0.84(t, 3H, J=7.2Hz) 1.80(tq, 2H, J=7.2Hz) 2.23(s, 3H) 4.38(t, 2H, J=7.2Hz) 5.99(d, 1H, J=8.4Hz) 6.45~6.75(s+m, 2H) 7.3~7.55(m, 1H) 7.55~7.75(m, 1H) 8.21(d, 1H, J=8.4Hz) 9.53(bs, 2H) | 172~ 174 |
| 1090 | CDCl$_3$ + DMSO d-6 | 0.84(t, 3H, J=7.2Hz)1.78(tq, 2H, J=7.2Hz) 2.23(s, 3H) 4.39(t, 2H, J=7.2Hz) 6.17(d, 1H, J=8.4Hz) 6.57(s, 1H) 7.05~7.4(m, 2H)7.4~7.55 (m, 1H) 8.23(d, 1H, J=8.4Hz) 9.52 (bs, 2H) | 190~ 194 |
| 1091 | CDCl$_3$ + DMSO d-6 | 1.44(d, 6H, J=6.6Hz) 2.27(s, 3H) 5.48(qq, 1H, J=6.6Hz) 6.17(d, 1H, J=7.8Hz) 6.35~6.75(m, 2H) 6.05(s, 1H) 7.15~7.65(m, 1H) 8.30(d, 1H, J=7.8Hz) 9.50(bs, 1H)9.78(bs, 1H) | 181~ 183 |
| 1092 | CDCl$_3$ + DMSO d-6 | 1.44(d, 6H, J=6.6Hz) 2.28(s, 3H) 5.46(qq, 1H, J=6.6Hz) 6.34(d, 1H, J=7.8Hz) 6.60(s, 1H) 6.90~7.20(m, 1H) 7.20~7.50(m, 2H) 8.33(d, 1H, J=7.8Hz) 9.62(bs, 2H) | 209~ 210 |
| 1093 | CDCl$_3$ + DMSO d-6 | 1.44(d, 6H, J=6.6Hz), 2.28(s, 3H) 5.46(qq, 1H, J=6.6Hz) 6.01(d, 1H, J=7.8Hz) 6.50~6.80(m, 2H) 7.40~7.60(m, 1H) 8.23(d, 1H, J=7.8Hz) 9.48(bs, 1H) 9.61(bs, 1H) | 191~ 193 |
| 1094 | CDCl$_3$ + DMSO d-6 | 1.44(d, 6H, J=6.6Hz), 2.22(s, 3H) 5.36(qq, 1H, J=6.6Hz) 6.18(d, 1H, J=7.8Hz) 6.31(s, 1H), 6.80~7.25(m, 2H) 7.25~7.60(m, 2H) | 138~ 141 |
| 1096 | CDCl$_3$ + DMSO d-6 | 1.44(d, (6H), J=6Hz) 5.38(qq, (1H), J=6Hz) 6.15(d, (1H), J=7.8Hz) 6.62 (d, (1H), J=1.8Hz) 6.71-6.97(m, (1H), 7.00 -7.28(m, (2H)) 7.33(d, (1H), J=1.8Hz) 8.16(d, (1H), J=7.8Hz) 9.25(brs, (1H)) 9.37(brs, (1H)) | 155~ 157 |
| 1097 | CDCl$_3$ + DMSO d-6 | 1.42(d,J=6.6Hz, 6H), 5.38(qq, J=6.6Hz, 1H), 5.85(d, J=8.4Hz, 1H), 6.37-6.61(m, 1H), 6.63(d, J=1.8Hz, 1H), 7.17-7.28(m, 1H), 7.32(d, J=1.8Hz, 1H), 7.42-7.58(m, 1H), 8.03(d, J=8.4Hz, 1H), 9.13(brs, 1H), 9.23(brs, 1H) | 151~ 154 |
| 1098 | CDCl$_3$ + DMSO d-6 | 1.42(d, (6H), J=7.2Hz) 5.40(qq, (1H), J=20 Hz) 6.00(d, (1H), J=7.8Hz) 6.64(d, (1H), J=1.8Hz) 6.92-7.56(m, (4H)) 8.13(d, (1H), J=7.8Hz) 9.20 (brs, (2H)) | 166~ 170 |
| 1099 | CDCl$_3$ + DMSO d-6 | 0.50~0.90(m, 3H), 1.38(d, 3H, J=7.2Hz) 1.50~2.10(m, 2H), 2.21 (s, 3H) 4.75~5.40(m, 1H), 6.12(d, 1H, J=7.2Hz) 6.34(s, 1H), 6.65~6.95(m, 1H) 6.95~7.25(m, 2H) 8.00(d, 1M, J=7.2Hz) 9.24(brs, 1H) | 168~ 170 |
| 1100 | CDCl$_3$ + DMSO d-6 | 0.80(d, 3H, J=6.6Hz), 2.18(s, 3H) 1.80~2.35(m, 1H), 4.19(d, 2H, J=7.2Hz) 6.10(d, 1H, J=7.2Hz) 6.45(s, 1H) 6.70~6.95(m, 1H), 7.00(m, 2H) 8.16(d, 1H, J=7.2Hz) 9.32(brs, 1H), 9.60(brs, 1H) | 203~ 204 |
| 1118 | DMSO d-6 | 1.60~1.88(m, 2H), 2.27(s, 3H) 1.99~2.44(m, 4H), 5.52(quint, 1H, J=8.3Hz), 6.20(d, 1H, J=8.1Hz) 6.69(s, 1H), 7.00~7.08(m, 1H) 7.22~7.29(m, 1H), 7.42~7.51(m, 1H) 8.43(d, 1H, J=8.1Hz), 9.53(brs, 1H) 9.83(brs, 1H) | 201~ 205 (de- comp.) |
| 1119 | DMSO d-6 | 1.34~2.18(m, 8H), 2.25(s, 3H) 5.30~5.88(m, 1H), 6.30(d, 1H, J=8.4Hz) 6.64(s, 1H), 6.92~7.18 (m, 1H) 7.22~7.55(m, 2H), 8.33(d, 1H, J=8.4Hz) 9.53(brs, 1H), 9.70(brs, 1H) | 165~ 180 (de- comp.) |
| 1122 | CDCl$_3$ + | 0.15~0.60(m, 4H), 0.95~1.55(m, 1H) 2.18(s, 3H), 4.23(d, 2H, J=7.2Hz) | 172~ 173 |

TABLE 4-continued

| Compound No. | Solvent | ppm (Standard TMS) | M.P. (°C.) |
|---|---|---|---|
| | DMSO d-6 | 5.93(d, 1H, J=7.2Hz) 6.20~6.50(m, 2H), 6.61(s, 1H) 7.35~7.55(m, 1H), 8.37(d, 1H, J=7.2Hz) 9.31(brs, 1H), 9.73(brs, 1H) | |
| 1123 | CDCl$_3$ + DMSO d-6 | 0.15~0.60(m, 4H), 0.90~1.50(m, 1H) 2.18(s, 3H), 4.22(d, 2H, J=6.6Hz) 6.08(d, 1H, J=7.8Hz), 6.49(s, 1H) 6.70~6.95(m, 1H), 6.95~7.30(m, 2H) 8.22(d, 1H, J=7.8Hz), 9.35(brs, 1H) 9.65(brs, 1H) | 187~ 190 |
| 1124 | CDCl$_3$ + DMSO d-6 | 0.20~0.65(m, 4H), 0.90~1.55(m, 1H) 2.18(s, 3H), 4.23(d, 2H, J=7.2Hz) 5.83(d, 1H, J=7.2Hz) 6.45~6.60(m, 1H), 6.55(s, 1H) 7.30~7.45(m, 1H), 7.50~7.65(m, 1H) 8.20(d, 1H, J=7.2Hz), 9.25(brs, 1H) 9.56(brs, 1H) | 192~ 194 |
| 1125 | CDCl$_3$ + DMSO d-6 | 0.10~0.60(m, 4H), 0.95~1.55(m, 1H) 2.19(s, 3H), 4.23(d, 2H, J=7.2Hz) 5.93(d, 1H, J=7.2Hz), 6.50(s, 1H) 7.00~7.50(m, 3H), 8.19(d, 1H, J=7.2Hz) 9.27(brs, 1H), 4.50(brs, 1H) | 207~ 209 |
| 1135 | CDCl$_3$ + DMSO d-6 | 1.48(d, 3h), 2.22(s, 3H) 3.45~4.10(m, 2H), 5.25~5.70(m, 1H) 6.13(d, 1H, J=7.8Hz), 6.45(s, 1H) 6.70~6.95(m, 1H), 7.00~7.30(m, 2H) 9.19(d, 1H, J=7.8Hz), 9.31(brs, 1H) 9.49(brs, 1H) | 178~ 180 |
| 1157 | CDCl$_3$ + DMSO d-6 | 1.40~2.78 (m, 6H), 2.64(s, 3H), 5.48(q, 1H) 5.80(d, 1H, J=8.4Hz) 6.21~6.64 (m, 2H), 7.12~7.37(m, 1H) 7.37~7.61(m, 1H), 7.98(d, 1H, J=8.4Hz) 9.18(brs, 1H), 9.37(brs, 1H) | 193~ 195 |
| 1161 | DMSO d-6 | 1.46~2.12(m, 8H), 2.19(s, 3H) 5.14~5.70(m, 1H), 5.96(d, 1H, J=8.4Hz) 6.64(s, 1H), 7.08~7.34(m, 1H) 7.35~7.72(m, 2H), 8.40(d, 1H, J=8.4Hz) 9.43(brs, 1H), 9.70(brs, 1H) | 155~ 160 (decomp.) |

In addition, the present invention further provides a fungicide for agricultural and horticultural use which is characterized by containing the amido-substituted derivative as represented by the above-mentioned general formula (I) of the present invention, as an active ingredient.

The fungicide for agricultural and horticultural use of the present invention is effective not only against Pseudoperonospora-caused diseases and Phytophthora-caused diseases of various crops but also against other various fungous diseases of various crops. As typical fungous diseases against which the fungicide of the present invention is effective, there may be mentioned, for example, *Pseudoperonospora cubensis, Plasmopara viticola, Bremia lacducae, Peronospora brassicae, Pseudoperonospora humuli, Phytophthora infestans, Phytophthora capsici* (cucumber and green pepper), tomato, cucumber and rice plant damping-off diseases caused by Pythium fungi as well as beet plant damping-off diseases caused by Aphanomyces fungi.

For application of the fungicide of the present invention to crops, the fungicide can be applied to crops by means of seed treatment, foliage treatment and soil treatment. The amount of the fungicide and the concentration thereof to be actually applied to crops vary in accordance with the crops to be treated, the diseases to be protected against, the degree of the occurrence of the diseases, the method of the application of the fungicide, etc. Accordingly, when the fungicide is to be applied over crops, the amount of the active ingredient may be from 2 to 2000 g/ha, preferably from 10 to 1000 g/ha.

The concentration of the fungicide to be applied may be from 1 to 1000 ppm, preferably from 5 to 500 ppm.

Since the fungicide for agricultural and horticultural use of the present invention has both a preventive effect and a curative effect, it may be applied over crops either for prevention of diseases before the crops are infected or for cure of the diseases of crops after the crops have been infected, and therefore, the proper time for applying the fungicide of the present invention may be wide and broad.

The fungicide of the present invention can be used, if desired, in combination with other biological active compounds, for example, agricultural chemicals such as the similar or complementary fungicides, or insecticides, herbicides, plant growth regulators, etc., and fertilizer substances, soil improving agents and the like. It is a matter of course that the fungicide of the present invention can be formed into a preparation together with the biological active compounds, if desired.

The phytopathogenic fungicide of the present invention can be used in combination with a suitable carrier, for example, a solid carrier such as clay, talc, bentonite, diatomaceous earth, etc., or a liquid carrier such as water, alcohols (e.g., methanol, ethanol, etc.), aromatic hydrocarbons (e.g., benzene, toluene, xylene, etc.), chlorinated hydrocarbons, ethers, ketones, esters (e.g., ethyl acetate, etc.), acid amides (e.g., dimethylformamide, etc.), etc., and if desired, an emulsifier, a dispersing agent, a suspension promoter, a permeation promoter, a spreader, a stabilizier, etc. can be added to form preparations in the form of an emulsifiable concentrate, oil solutions, wettable powders, dusts, granulars, flowables, etc. for practical use.

Examples of formulations of compositions of the phytopathogenic fungicide of the present invention are mentioned hereunder, in which the kinds of ingredients and the amounts thereof are concretely described. Needless to say, these examples do not whatsoever limit the scope of the present invention. The "parts" means "parts by weight" in the formulations, unless otherwise specifically stated.

| (1) Wettable Powders: | |
| --- | --- |
| The compound of the invention | 5 to 75 parts |
| Solid carrier | 9 to 86 parts |
| Surfactant | 5 to 10 parts |
| Others | 1 to 5 parts |

As the solid carrier, there may be mentioned calcium carbonate, kaolinite, Zeeklite A, Zeeklite PFP, diatomaceous earth, talc, etc.

As the surfactant, there may be mentioned Lunox 1000C, Sorpol 5039, Sorpol 5050, Sorpol 005D Sorpol 5029-O, calcium sulfonate, sodium dodecylsulfonate, etc.

Other components include Carplex #80, etc.

| (2) Emulsifiable concentrate: | |
| --- | --- |
| The compound of the invention | .5 to 50 parts |
| Liquid Carrier | 35 to 90 parts |
| Surfactant | 5 to 15 parts |

As the liquid carrier, there may be mentioned xylene, dimethylformamide, methylnaphthalene, isophorone, etc.

As the surfactant, there may be mentioned Sorpol 2680, Sorpol 3005X, Sorpol 3346, etc.

| (3) Flowables: | |
| --- | --- |
| The compound of the invention | 5 to 75 parts |
| Liquid carrier | 14.5 to 68 parts |
| Surfactant | 5 to 10 parts |
| Others | 5 to 10 parts |

As the liquid carrier, water can be used.

As the surfactant, there may be mentioned Lunox 1000C, Sorpol 3353, Sorpol FL, Nippol, Agrisol S-710, sodium ligninsulfonate, etc.

Others include ethylene glycol, propylene glycol, Xanthan gum, etc.

| (4) Dusts: | |
| --- | --- |
| The compound of the invention | 0.03 to 3 parts |
| Solid carrier | 94 to 98.97 parts |
| Others | 1 to 3 parts |

As the solid carrier, there may be mentioned calcium carbonate, kaolinite, Zeeklite, talc, etc.

Others include diisopropyl phosphate, Carplex #80, etc.

| (5) Granulars: | |
| --- | --- |
| The compound of the invention | 0.3 to 10 parts |
| Solid carrier | 92 to 98.7 parts |
| Others | 1 to 5 parts |

As the solid carrier, there may be mentioned calcium carbonate, kalinite, bentonite, talc, etc.

Others include calcium ligninsulfonate, polyvinyl alcohol, etc.

Next, concrete examples of formulations of fungicides containing the substituted-amido derivatives of the formula (I) of the present invention are mentioned hereunder, which, however, are not intended to limit the scope of the present invention. In the formulations, "parts" means "parts by weight", unless otherwise specifically defined.

| Formulation example 1: Wettable Powders | |
| --- | --- |
| The compound of the invention | 5 parts |
| Zeeklite PFP | 87 parts |
| (Mixture of kaolinite and sericite, trade name by Zeeklite Co., Ltd.) | |
| Sorpol 5039 | 5 parts |
| (Mixture of anionic surfactant and white carbon, trade name by Toho Chemical Industrial Co.) | |
| Carplex #80 | 3 parts |
| (White carbon, trade name by Shionogi & Co.) | |

The above ingredients were uniformly blended and powdered to form wettable powders. For the practical use, the wettable powders are diluted to form a 1/100 to 1/10,000 solution, and this is applied in an amount of from 10 to 1000 g/ha, as the active ingredient.

| Formulation example 2: Wettable Powders | |
| --- | --- |
| The compound of the invention | 25 parts |
| Zeeklite PFP | 69 parts |
| (Mixture of kaolinite and sericite, trade name by Zeeklite Co. Ltd.) | |
| Sorpol 5039 | 3 parts |
| (Mixture of anionic surfactant and white carbon, trade name by Toho Chemical Industrial Co.) | |
| Carplex #80 | 3 parts |
| (White carbon, trade name by Shionogi & Co.) | |

The above ingredients were uniformly blended and powdered to form wettable powders. For the practical use, the wettable powders are diluted to form a 1/500 to 1/50,000 solution, and this is sprayed in the amount of from 10 to 1000 g/ha, as the active ingredient.

| Formulation example 3: Wettable Powders | |
| --- | --- |
| The compound of the invention | 20 parts |
| Calcium carbonate (powder) | 69 parts |
| Sorpol 5050 | 10 parts |
| (Mixture of anionic surfactant and white carbon, trade name by Toho Chemical Industrial Co.) | |
| Carplex #80 | 1 part |
| (White carbon, trade name by Shionogi & Co.) | |

The above ingredients were uniformly blended and powdered to form wettable powders. For the practical use, the wettable powders are diluted to form a 1/1,500 to 1/150,000 solution, and this is sprayed in an amount of from 10 to 100 g/ha, as the active ingredient.

| Formulation example 4: Emulsifiable concentrate | |
|---|---|
| The compound of the invention | 5 parts |
| Xylene | 70 parts |
| N,N-dimethylformamide | 20 parts |
| Sorpol 2680 | 5 parts |
| (Mixture of non-ionic surfactant and anionic surfactant, trade name by Toho Chemical Industrial Co.) | |

The above ingredients were uniformly blended to form an emulsifiable concentrate. For the practical use, the emulsifiable concentrate is diluted into a 1/100 to 1/10,000 emulsion, and this is sprayed in an amount of from 10 to 1000 g/ha, as the active ingredient.

| Formulation example 5: Emulsifiable concentrate | |
|---|---|
| The compound of the invention | 50 parts |
| Xylene | 25 parts |
| N,N-dimethylformamide | 10 parts |
| Sorpol 3346 | 15 parts |
| (Mixture of non-ionic surfactant and anionic surfactant, trade name by Toho Chemical Industrial Co.) | |

The above ingredients were uniformly mixed to form an emulsifiable concentrate. For the practical use, the emulsion concentrate is diluted into a 1/1,000 to 1/100,000 emulsion, and this is applied in an amount of from 10 to 1000 g/ha, as the active ingredient.

| Formulation example 6: Flowables | |
|---|---|
| The compound of the invention | 5 parts |
| Sorpol | 5 parts |
| (Non-ionic surfactant, trade name by Toho Chemical Industrial Co.) | |
| Lunox 1000C | 3 parts |
| (Anionic surfactant, trade name by Toho Chemical Industrial Co.) | |
| 1% Aqueous solution of Xanthan gum | 20 parts |
| (Natural high molecular substance) | |
| Water | 57 parts |
| Ethylene glycol | 10 parts |

The above-mentioned ingredients, except the active ingredient (the compound of the invention), were uniformly dissolved, and then the compound of the invention was added thereto and stirred well, and thereafter the resulting mixture was wet-milled in a sand mill, to obtain flowables. For the practical use, the flowables are diluted into a 1/100 to 1/10,000 solution, and this is applied in an amount of from 10 to 1000 g/ha, as the active ingredient.

| Formulation example 7: Flowables | |
|---|---|
| The compound of the invention | 75 parts |
| Sorpol 3353 | 5 parts |
| (Non-ionic surfactant, trade name by Toho Chemical Industrial Co.) | |
| Lunox 1000C | 0.5 parts |
| (Anionic surfactant, trade name by Toho Chemical Industrial Co.) | |
| 1% Aqueous solution of Xanthan gum | 10 parts |
| (Natural high molecular substance) | |
| Water | 4.5 parts |

| Formulation example 7: Flowables | |
|---|---|
| Propylene glycol | 5 parts |

The above-mentioned ingredients, except the active ingredient (the compound of the invention), were uniformly dissolved, and then the compound of the invention was added thereto and stirred well, and thereafter the resulting mixture was wet-milled in a sand mill, to obtain flowables. For the practical use, the flowables are diluted into a 1/1,500 to 1/150,000 solution, and this is applied in an amount of from 10 to 1000 g/ha, as the active ingredient.

| Formulation example 8: Dust | |
|---|---|
| The compound of the invention | 10 parts |
| Clay | 90 parts |

The above ingredients were uniformly blended to obtain dust. For the practical use, this may be applied in an amount of from 10 to 1000 g/ha, as the active ingredient.

| Formulation example 9: Granulars | |
|---|---|
| The compound of the invention | 5 parts |
| Bentonite | 25 parts |
| Talc | 70 parts |

The above ingredients were uniformly mixed and ground and then a small amount of water was added thereto and stirred and kneaded. The resulting mixture was granulated from an extrusion granulator and dried to obtain granulars.

For the practical use, the granulars may be sprayed in an amount from 10 to 1000 g/ha, as the active ingredient.

Next, the effect of the compounds of the present invention is concretely described hereinafter by reference to biological tests.

Test Example 1

(1) Test of preventive efficacy against *Pseudoperonospora cubensis*

When cucumber plants (cultivar: Sagami-hanjiro), which were growing in pots each having a diameter of 7 cm, became 1- to 2-leaf state, the compound of the present invention, which was in the form of the emulsion concentrate as formed in accordance with the above-mentioned formulation example 1 and which was diluted with water to 500 ppm, was sprayed thereover with a gun type sprayer in an amount of 20 ml/pot. Next day after the spraying, a suspension of spores of *Pseudoperonospora cubensis* ($2 \times 10^5$/ml) was sprayed over the plants, and the pots were put in an inoculation box kept at a temperature of 25° C. and a humidity of 95% or more for a whole day and night. Afterwards, the pots were put in a greenhouse, and the 7th day after the inoculation, the proportion of the diseased area on the leaf in each plant was measured. The protective value was calculated on the basis of the following formula:

$$\text{Protective Value} = \left\{ 1 - \frac{\text{Proportion of diseased area on the leaves of test plants}}{\text{Proportion of diseased area on the leaves of control plants}} \right\} \times 100$$

The test results obtained are shown in Table 5 below.

TABLE 5

(Concentration on treatment: 500 ppm)

| Compound No. | Inhibitory Value | Compound No. | Inhibitory Value |
|---|---|---|---|
| 27 | 100 | 1089 | 100 |
| 36 | 100 | 1090 | 100 |
| 47 | 100 | 1091 | 100 |
| 81 | 100 | 1092 | 100 |
| 92 | 100 | 1093 | 100 |
| 739 | 100 | 1094 | 100 |
| 763 | 100 | 1096 | 100 |
| 766 | 100 | 1097 | 100 |
| 824 | 100 | 1098 | 100 |
| 825 | 100 | 1099 | 100 |
| 1075 | 100 | 1100 | 100 |
| 1076 | 100 | 1118 | 100 |
| 1077 | 100 | 1119 | 100 |
| 1078 | 100 | 1122 | 100 |
| 1080 | 100 | 1123 | 100 |
| 1081 | 100 | 1124 | 100 |
| 1082 | 100 | 1125 | 100 |
| 1083 | 100 | 1135 | 100 |
| 1084 | 100 | 1157 | 100 |
| 1085 | 100 | 1161 | 100 |
| 1086 | 100 | Zineb | 65 |
| 1087 | 100 | Compound A | 100 |
| 1088 | 100 | Compound B | 100 |
|  |  | Compound C | 100 |

The "zineb" in Table 5 is Dithane as a trade name, or zinc ethylene-bis-dithiocarbamate as a chemical name. The Compound A; Compound B and Compound C are control compounds as mentioned hereinafter.

Test Example 2

(2) Test of preventive efficacy against *Pseudoperonospora cubensis*

The procedure of Test example 1 was repeated, except that the concentration of the compound in the agent to be applied to plants was varied from 500 ppm to 100 ppm. The test results obtained are shown in Table 6 below.

TABLE 6

(Concentration on treatment: 100 ppm)

| Compound No. | Inhibitory Value | Compound No. | Inhibitory Value |
|---|---|---|---|
| 27 | 100 | 1088 | 100 |
| 36 | 100 | 1089 | 100 |
| 47 | 100 | 1090 | 100 |
| 81 | 100 | 1091 | 100 |
| 92 | 100 | 1092 | 100 |
| 739 | 100 | 1093 | 100 |
| 763 | 100 | 1094 | 100 |
| 766 | 100 | 1096 | 100 |
| 824 | 100 | 1097 | 100 |
| 825 | 100 | 1098 | 100 |
|  |  | 1099 | 100 |
| 1075 | 100 | 1100 | 100 |
| 1076 | 100 | 1118 | 100 |
| 1077 | 100 | 1119 | 100 |
| 1078 | 100 | 1122 | 100 |
| 1080 | 100 | 1123 | 100 |
| 1081 | 100 | 1124 | 100 |
| 1082 | 100 | 1125 | 100 |
| 1083 | 100 | 1135 | 100 |
| 1084 | 100 | 1157 | 100 |
| 1085 | 100 | 1161 | 100 |
| 1086 | 100 | Zineb | 0 |
| 1087 | 100 | Compound A | 90 |
|  |  | Compound B | 100 |
|  |  | Compound C | 0 |

Test Example 3

(1) Test of curative efficacy against *Pseudoperonospora cubensis*

When cucumber plants (cultivar: Sagami-hanjiro), which were growing in pots each having a diameter of 7 cm, became 1- to 2-leaf stage, a suspension of spores of *Pseudoperonospora cubensis* ($2 \times 10^5$/ml) was applied thereover, and the pots were put in an inoculation box kept at a temperature of 25° C. and a humidity of 95% or more for a whole day and night for inoculation of the spores to the plants. The next day, the compound of the present invention, which was in the form of the emulsifiable concentrate as formed in accordance with the above-mentioned formulation example 1 and which was diluted with water to 500 ppm, was applied over the plants with a gun type sprayer in an amount of 20 ml/pot. Afterwards, the pots were put in a greenhouse, and the 7th day after the inoculation, the proportion of the diseased area on the leaf in each plant was measured. The protective value was calculated on the basis of the following formula:

$$\text{Protective Value} = \left\{ 1 - \frac{\text{Proportion of diseased area on the leaves of test plants}}{\text{Proportion of diseased area on the leaves of control plants}} \right\} \times 100$$

The test results obtained are shown in Table 7 below.

TABLE 7

(Concentration on treatment: 500 ppm)

| Compound No. | Inhibitory Value | Compound No. | Inhibitory Value |
|---|---|---|---|
| 27 | 100 | 1089 | 100 |
| 36 | 100 | 1090 | 100 |
| 47 | 100 | 1091 | 100 |
| 81 | 100 | 1092 | 100 |
| 92 | 100 | 1093 | 100 |
| 739 | 100 | 1094 | 100 |
| 763 | 100 | 1096 | 100 |
| 766 | 100 | 1097 | 100 |
| 824 | 100 | 1098 | 100 |
| 825 | 100 | 1099 | 100 |
| 1075 | 100 | 1100 | 100 |
| 1076 | 100 | 1118 | 100 |
| 1077 | 100 | 1119 | 100 |
| 1078 | 100 | 1122 | 100 |
| 1080 | 100 | 1123 | 100 |
| 1081 | 100 | 1124 | 100 |
| 1082 | 100 | 1125 | 100 |
| 1083 | 100 | 1135 | 100 |
| 1084 | 100 | 1157 | 100 |
| 1085 | 100 | 1161 | 100 |
| 1086 | 100 | Zineb | 0 |
| 1087 | 100 | Compound A | 100 |

TABLE 7-continued (Concentration on treatment: 500 ppm)

| Compound No. | Inhibitory Value | Compound No. | Inhibitory Value |
| --- | --- | --- | --- |
| 1088 | 100 | Compound B | 100 |
|  |  | Compound C | 50 |

Test Example 4

(2) Cure test for *Pseudoperonospora cubensis*

The procedure of Test example 3 was repeated, except that the concentration of the compound in the agent to be applied to plants were varied from 500 ppm to 100 ppm. The test results obtained are shown in Table 8 below.

TABLE 8

(Concentration on treatment: 100 ppm)

| Compound No. | Inhibitory Value | Compound No. | Inhibitory Value |
| --- | --- | --- | --- |
| 27 | 100 | 1089 | 100 |
| 36 | 100 | 1090 | 100 |
| 47 | 100 | 1091 | 100 |
| 81 | 100 | 1092 | 100 |
| 92 | 100 | 1093 | 100 |
| 739 | 100 | 1094 | 100 |
| 763 | 100 | 1096 | 100 |
| 766 | 100 | 1097 | 100 |
| 824 | 100 | 1098 | 100 |
| 825 | 100 | 1099 | 100 |
| 1075 | 100 | 1100 | 100 |
| 1076 | 100 | 1118 | 100 |
| 1077 | 100 | 1119 | 100 |
| 1078 | 100 | 1122 | 100 |
| 1080 | 100 | 1123 | 100 |
| 1081 | 100 | 1124 | 100 |
| 1082 | 100 | 1125 | 100 |
| 1082 | 100 | 1135 | 100 |
| 1083 | 100 | 1157 | 100 |
| 1084 | 100 | 1161 | 100 |
| 1085 | 100 | Zineb | 0 |
| 1086 | 100 | Compound A | 78 |
| 1087 | 100 | Compound B | 100 |
| 1088 | 100 | Compound C | 0 |

Test Example 5

Test of chemical phytotoxicity

The compound of the present invention, which was in the form of the emulsion concentrate as formed in accordance with the above-mentioned formulation Example 1 and which was adjusted to have a desired concentration, was sprayed over cucumber plants (Sagami-hanjiro 2- to 3-leaf stage), which were growing in pots each having a diameter of 7 cm, with a gun type sprayer in an amount of 20 ml/pot. The cucumber plants were further grown in a greenhouse for 7 days, and the degree of the test of chemical phytotoxicity of each plant was investigated on the basis of the following evaluation standard.

Evaluation Standard:
5: Completely died.
4: Growth was remarkably inhibited and the plants partly died.
3: Growth was remarkably inhibited.
2: Growth was somewhat inhibited.
1: Growth was slightly inhibited.
0: Growth was normal.

The test results obtained are shown in Table 9 below.

TABLE 9

| Compound No. | 500 | 100 | 50 (ppm) |
| --- | --- | --- | --- |
| 2 7 | 0 | 0 | 0 |
| 3 6 | 0 | 0 | 0 |
| 9 2 | 0 | 0 | 0 |
| 7 3 9 | 0 | 0 | 0 |
| 7 6 3 | 0 | 0 | 0 |
| 7 6 6 | 0 | 0 | 0 |
| 8 2 4 | 0 | 0 | 0 |
| 8 2 5 | 0 | 0 | 0 |
| Referential Compound A | 3 | 3 | 2 |
| Referential Compound B | 3 | 3 | 3 |
| Referential Compound C | 3 | 2 | 2 |
| 1075 | 0 | 0 | 0 |
| 1076 | 0 | 0 | 0 |
| 1077 | 0 | 0 | 0 |
| 1085 | 0 | 0 | 0 |
| 1086 | 0 | 0 | 0 |
| 1087 | 0 | 0 | 0 |
| 1088 | 0 | 0 | 0 |
| 1089 | 0 | 0 | 0 |
| 1090 | 0 | 0 | 0 |
| 1091 | 0 | 0 | 0 |
| 1092 | 0 | 0 | 0 |
| 1093 | 0 | 0 | 0 |
| 1094 | 0 | 0 | 0 |
| 1099 | 0 | 0 | 0 |
| 1100 | 0 | 0 | 0 |
| 1122 | 0 | 0 | 0 |
| 1123 | 0 | 0 | 0 |
| 1124 | 0 | 0 | 0 |
| 1125 | 0 | 0 | 0 |
| 1135 | 0 | 0 | 0 |

Compound A

Described in Japanese Patent Laid-Open Application No. 255759/85.

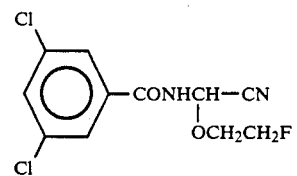

Compound B

Described in Japanese Patent Laid-Open Application No. 69866/83 (U.S. Pat. No. 4,515,959 (Table 1, Compound No. 5))

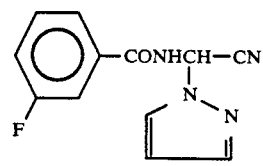

Compound C

Described in Japanese Patent Laid-Open Application No. 167978/82 (U.S. Pat. No. 4,432,784 (Table 1, Compound No. 23))

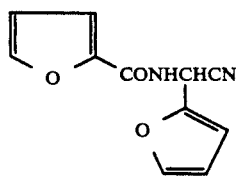

The above-mentioned biological test results apparently indicate that the compounds of the present invention have both a preventive effect and a curative effect and are noticeably effective against diseases caused by fungi of Phycomycetes, such as, for example, Pseudoperonospora cubensis-caused disease. In addition, the chemical phytotoxicity by the compounds of the present invention is little, as opposed to the other known compounds A to C.

While the invention has been described in detail and with reference to specific embodiments thereof, it will be apparent to one skilled in the art that various changes and modifications can be made therein without departing from the spirit and scope thereof.

What is claimed is:

1. An amide derivative represented by a formula (I):

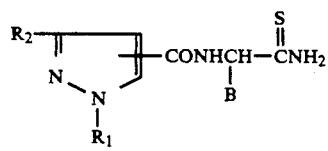

in which

R$_1$ represents an alkyl group having from 1 to 10 carbon atoms, a cycloalkyl group having from 3 to 10 carbon atoms, a cycloalkyl alkyl group having from 4 to 10 carbon atoms, an alkenyl group having from 2 to 10 carbon atoms, a cycloalkenyl group having from 3 to 10 carbon atoms, an alkynyl group having 2 to 10 carbon atoms, a halogenated alkyl group having from 1 to 10 carbon atoms, a halogenated cycloalkyl alkyl group having from 3 to 10 carbon atoms, an alkoxyalkyl group having from 2 to 10 carbon atoms, epoxide, oxetane, tetrahydrofuran, tetrahydrothiophene, epoxide methyl, oxetane methyl, or tetrahydrofuran methyl;

R$_2$ represents a hydrogen atom, a methyl group, a methoxy group, a halogen atom or a halogenated methyl group; and B represents:

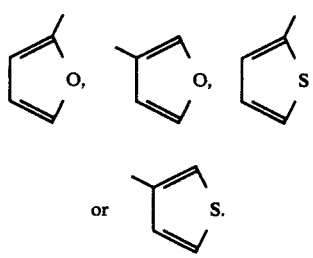

2. An amide derivative as claimed in claim 1, which is selected from the group consisting of:

(1)
1,3-Dimethyl-N-[3-thienyl(thiocarbamoyl)methyl]-1H-pyrazole-5-carboxamide

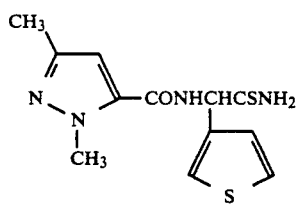

(2)
1-Ethyl-3-methyl-N-[2-thienyl(thiocarbamoyl)-methyl]-1H-pyrazole-5-carboxamide

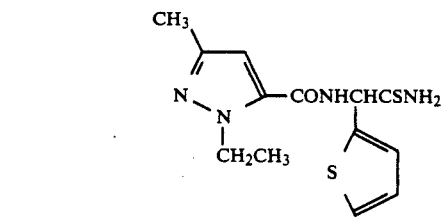

(3)
1-Isopropyl-3-methyl-N-[2-thienyl(thiocarbamoyl)-methyl]-1H-pyrazole-5-carboxamide

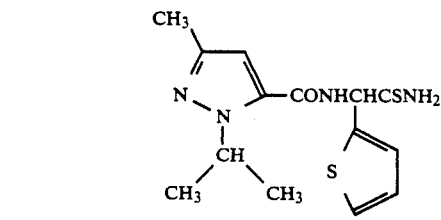

(4)
1-Cyclopropylmethyl-3-methyl-N-[2-thienyl(thiocarbamoyl)methyl]-1H-pyrazole-5-carboxamide

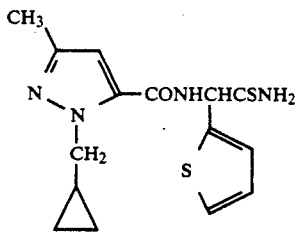

(5)
1-Isopropyl-3-methyl-N-[3-thienyl(thiocarbamoyl)-methyl]-1H-pyrazole-5-carboxamide

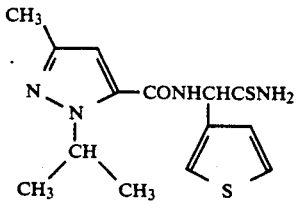

(6)
1-Isopropyl(-3-methyl-N-[2-furyl(thiocarbamoyl)-methyl]-1H-pyrazole-5-carboxamide

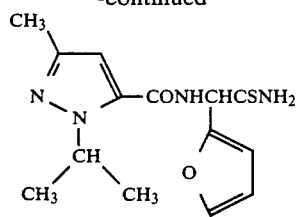

(7)
1-Isopropyl-3-methyl-N-[3-furyl(thiocarbamoyl)-methyl]-1H-pyrazole-5-carboxamide

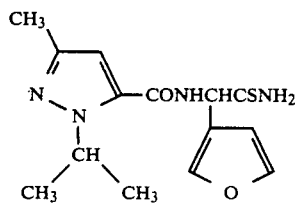

(8)
1-Ethyl-3-methyl-N-[3-thienyl(thiocarbamoyl)-methyl]-1H-pyrazole-5-carboxamide

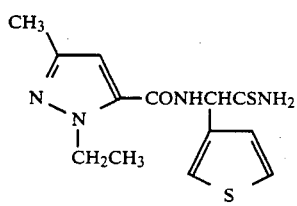

(9)
1-Ethyl-3-methyl-N-[2-furyl(thiocarbamoyl)-methyl]-1H-pyrazole-5-carboxamide

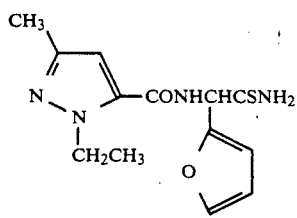

(10)
1-Ethyl-3-methyl-N-[3-furyl(thiocarbamoyl)-methyl]-1H-pyrazole-5-carboxamide

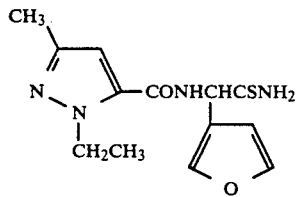

(11)
1,3-Dimethyl-N-[2-thienyl(thiocarbamoyl)-methyl]-1H-pyrazole-5-carboxamide

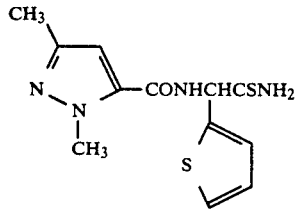

(12)
1-Cyclopropylmethyl-3-methyl-N-[3-thienyl-(thiocarbamoyl)methyl]-1H-pyrazole-5-carboxamide

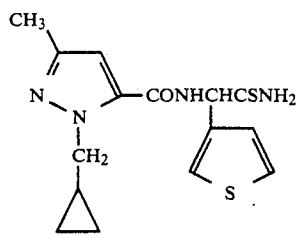

(13)
1-Cyclopropylmethyl-3-methyl-N-[2-furyl-(thiocarbamoyl)methyl]-1H-pyrazole-5-carboxamide

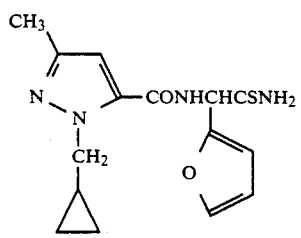

(14)
1-Cyclopropylmethyl-3-methyl-N-[3-furyl-(thiocarbamoyl)methyl]-1H-pyrazole-5-carboxamide

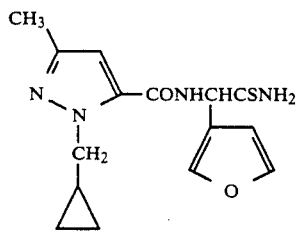

(15)
1-Cyclopropyl-3-methyl-N-[3-furyl-(thiocarbamoyl)-methyl]-1H-pyrazole-5-carboxamide

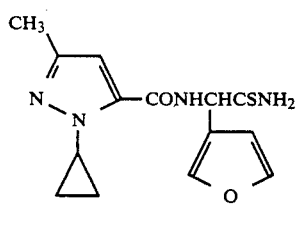

(16)
1-Cyclobutyl-3-methyl-N-[3-furyl-(thiocarbamoyl)-methyl]-1H-pyrazole-5-carboxamide

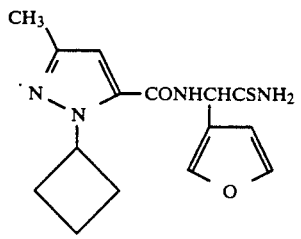

(17)
1-Cyclobutyl-3-methyl-N-[3-thienyl-(thiocarbamoyl)-methyl]-1H-pyrazole-5-carboxamide

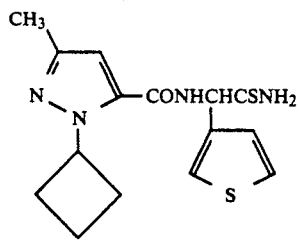

(18)
1-Cyclobutyl-3-methyl-N-[2-furyl-(thiocarbamoyl)-methyl]-1H-pyrazole-5-carboxamide

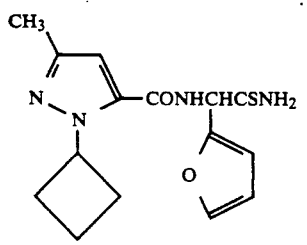

(19)
1-Cyclobutyl-3-methyl-N-[2-thienyl-(thiocarbamoyl)-methyl]-1H-pyrazole-5-carboxamide

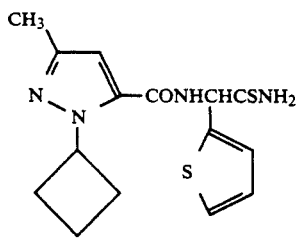

(20)
1-Cyclopentyl-3-methyl-N-[3-furyl-(thiocarbamoyl)-methyl]-1H-pyrazole-5-carboxamide

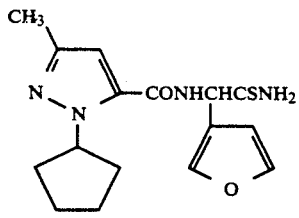

(21)
1-Cyclopentyl-3-methyl-N-[3-thienyl-(thiocarbamoyl)-methyl]-1H-pyrazole-5-carboxamide

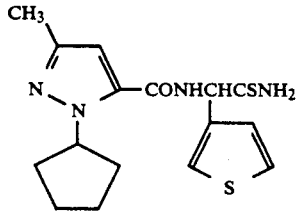

(22)
1-Cyclopentyl-3-methyl-N-[2-furyl-(thiocarbamoyl)-methyl]-1H-pyrazole-5-carboxamide

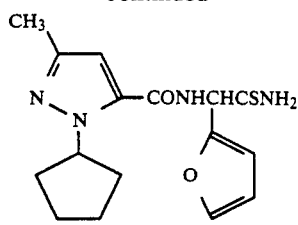

(23)
1-Cyclopentyl-3-methyl-N-[2-thienyl(thiocarbamoyl)-methyl]-1H-pyrazole-5-carboxamide

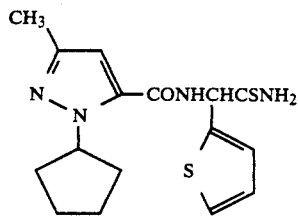

(24)
1-Cyclohexyl-3-methyl-N-[3-furyl-(thiocarbamoyl)-methyl]-1H-pyrazole-5-carboxamide

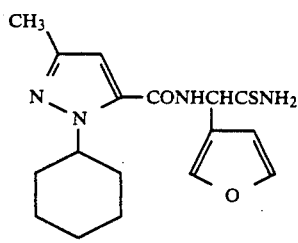

(25)
1-Cyclohexyl-3-methyl-N-[3-thienyl-(thiocarbamoyl)-methyl]-1H-pyrazole-5-carboxamide

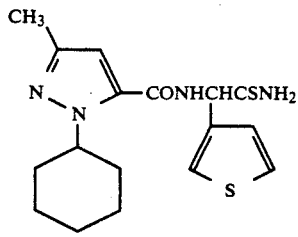

(26)
1-Cyclohexyl-3-methyl-N-[2-furyl(thiocarbamoyl)-methyl]-1H-pyrazole-5-carboxamide

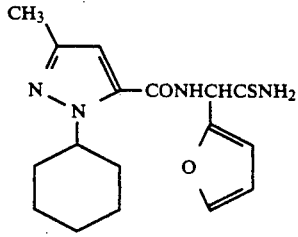

(27)
1-Cyclohexyl-3-methyl-N-[2-thienyl(thiocarbamoyl)-methyl]-1H-pyrazole-5-carboxamide

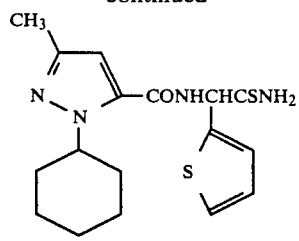

(28)
1-(2,3-epoxypropyl)-3-methyl-N-[3-furyl(thiocarbamoyl)-methyl]-1H-pyrazole-5-carboxamide

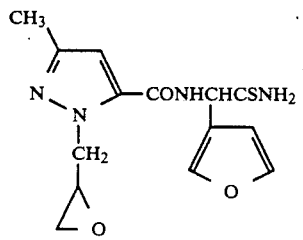

(29)
1-(2,3-epoxypropyl)-3-methyl-N-[3-thienyl(thiocarbamoyl)methyl]-1H-pyrazole-5-carboxamide

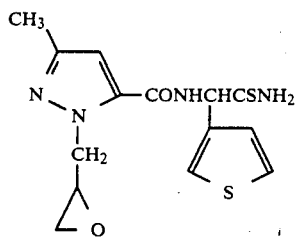

(30)
1-(2,3-epoxypropyl)-3-methyl-N-[2-furyl(thiocarbamoyl)-methyl]-1H-pyrazole-5-carboxamide

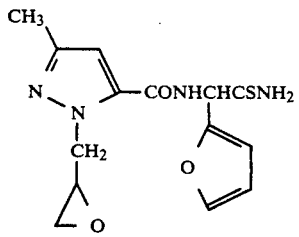

(31)
1-(2,3-epoxypropyl)-3-methyl-N-[2-thienyl(thiocarbamoyl)methyl]-1H-pyrazole-5-carboxamide

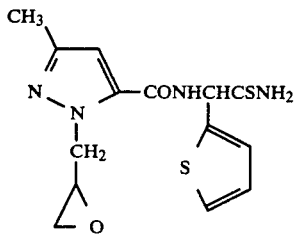

(32)
1-(3-tetrahydrothienyl)-3-methyl-N-[2-furyl(thiocarbamoyl)methyl]-1H-pyrazole-5-carboxamide

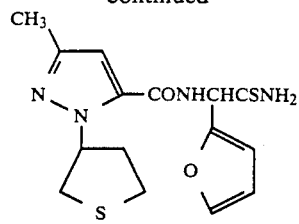

(33)
1-(3-cyclopentenyl)-3-methyl-N-[3-thienyl(thiocarbamoyl)methyl]-1H-pyrazole-5-carboxamide

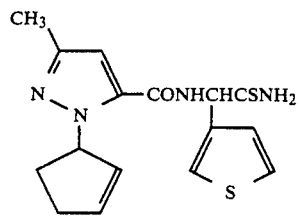

(34)
1-cyclopropyl-3-methyl-N-[2-furyl-(thiocarbamoyl)methyl]-1H-pyrazole-5-carboxamide

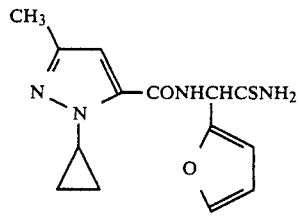

(35)
1-cyclopropyl-3-methyl-N-[2-thienyl-(thiocarbamoyl)methyl]-1H-pyrazole-5-carboxamide

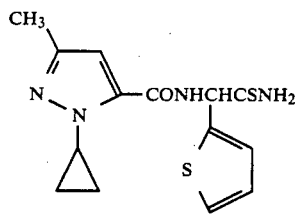

(36)
1-cyclopropyl-3-methyl-N-[3-thienyl-(thiocarbamoyl)methyl]-1H-pyrazole-5-carboxamide

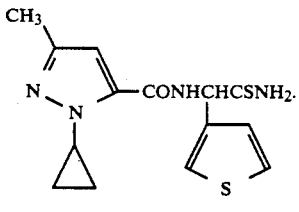

3. A phytopathogenic fungicide containing, as an active ingredient, a compound of formula (I):

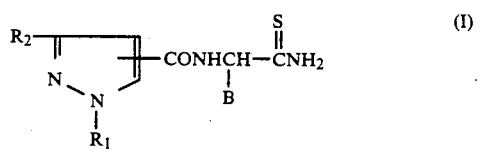

in which $R_1$ represents an alkyl group having from 1 to 10 carbon atoms, a cycloalkyl group having from 3 to 10 carbon atoms, a cycloalkyl alkyl group having from 4 to 10 carbon atoms, an alkenyl group having from 2 to 10 carbon atoms, a cycloalkenyl group having from 3 to 10 carbon atoms, an alkynyl group having 2 to 10 carbon atoms, a halogenated alkyl group having from 1 to 10 carbon atoms, a halogenated cycloalkyl alkyl group having from 3 to 10 carbon atoms, an alkoxyalkyl group having from 2 to 10 carbon atoms, epoxide, oxetane, tetrahydrofuran, tetrahydrothiophene, epoxide methyl, oxetane methyl, or tetrahydrofuran methyl;

$R_2$ represents a hydrogen atom, a methyl group, a methoxy group, a halogen atom or a halogenated methyl group; and B represents:

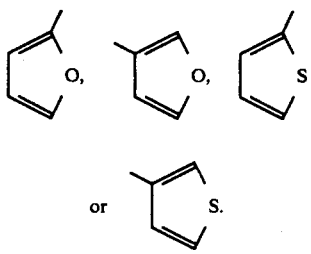

4. A phytopathogenic fungicide as claimed in claim 3, which contains, as an active ingredient, in a fungicidally acceptable carrier a compound selected from the group consisting of:

(1)
1,3-Dimethyl-N-[3-thienyl(thiocarbamoyl)methyl]-1H-pyrazole-5-carboxamide

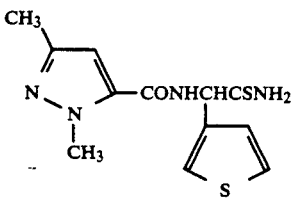

(2)
1-Ethyl-3-methyl-N-[2-thienyl(thiocarbamoyl)-methyl]-1H-pyrazole-5-carboxamide

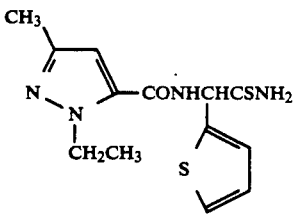

(3)
1-Isopropyl-3-methyl-N-[2-thienyl(thiocarbamoyl)-methyl]-1H-pyrazole-5-carboxamide

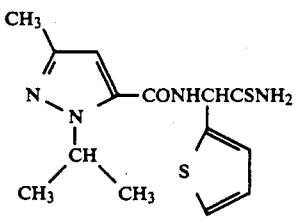

(4)
1-Cyclopropylmethyl-3-methyl-N-[2-thienyl(thiocarbamoyl)methyl]-1H-pyrazole-5-carboxamide

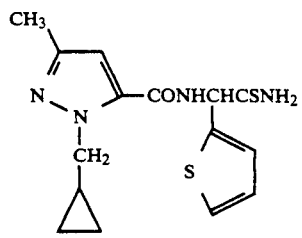

(5)
1-Isopropyl-3-methyl-N-[3-thienyl(thiocarbamoyl)-methyl]-1H-pyrazole-5-carboxamide

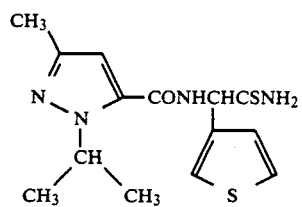

(6)
1-Isopropyl(-3-methyl-N-[2-furyl(thiocarbamoyl)-methyl]-1H-pyrazole-5-carboxamide

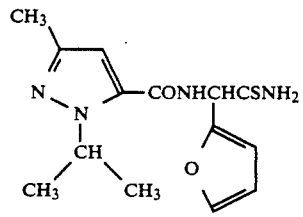

(7)
1-Isopropyl-3-methyl-N-[3-furyl(thiocarbamoyl)-methyl]-1H-pyrazole-5-carboxamide

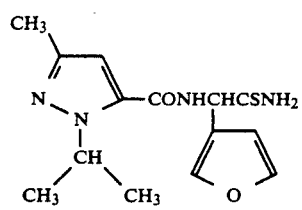

(8)
1-Ethyl-3-methyl-N-[3-thienyl(thiocarbamoyl)-methyl]-1H-pyrazole-5-carboxamide

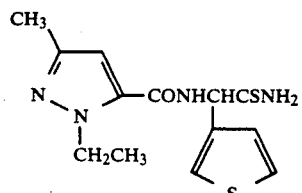

(9)
1-Ethyl-3-methyl-N-[2-furyl(thiocarbamoyl)-methyl]-1H-pyrazole-5-carboxamide

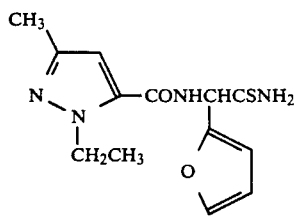

(10)
1-Ethyl-3-methyl-N-[3-furyl(thiocarbamoyl)-methyl]-1H-pyrazole-5-carboxamide

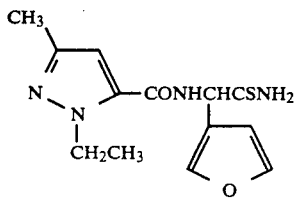

(11)
1,3-Dimethyl-N-[2-thienyl(thiocarbamoyl)-methyl]-1H-pyrazole-5-carboxamide

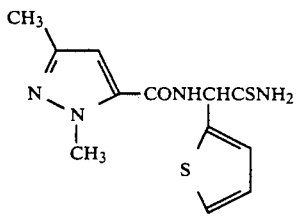

(12)
1-Cyclopropylmethyl-3-methyl-N-[3-thienyl-(thiocarbamoyl)methyl]-1H-pyrazole-5-carboxamide

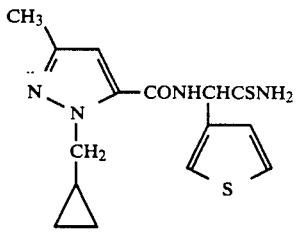

(13)
1-Cyclopropylmethyl-3-methyl-N-[2-furyl-(thiocarbamoyl)methyl]-1H-pyrazole-5-carboxamide

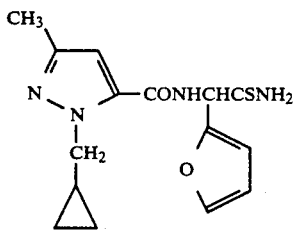

(14)
1-Cyclopropylmethyl-3-methyl-N-[3-furyl-(thiocarbamoyl)methyl]-1H-pyrazole-5-carboxamide

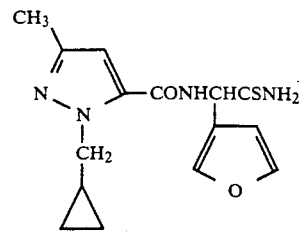

(15)
1-Cyclopropyl-3-methyl-N-[3-furyl-(thiocarbamoyl)-methyl]-1H-pyrazole-5-carboxamide

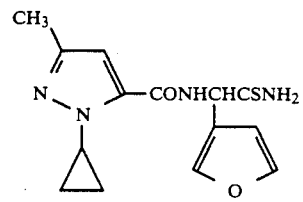

(16)
1-Cyclobutyl-3-methyl-N-[3-furyl-(thiocarbamoyl)-methyl]-1H-pyrazole-5-carboxamide

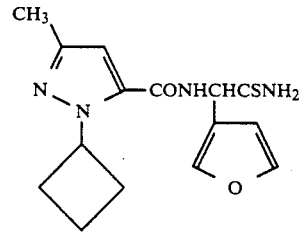

(17)
1-Cyclobutyl-3-methyl-N-[3-thienyl-(thiocarbamoyl)-methyl]-1H-pyrazole-5-carboxamide

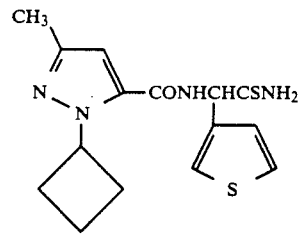

(18)
1-Cyclobutyl-3-methyl-N-[2-furyl-(thiocarbamoyl)-methyl]-1H-pyrazole-5-carboxamide

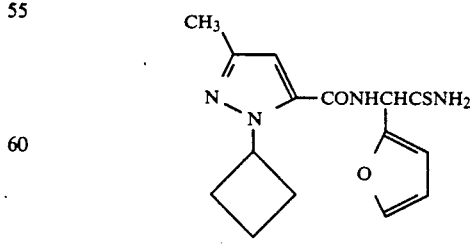

(19)
1-Cyclobutyl-3-methyl-N-[2-thienyl-(thiocarbamoyl)-methyl]-1H-pyrazole-5-carboxamide

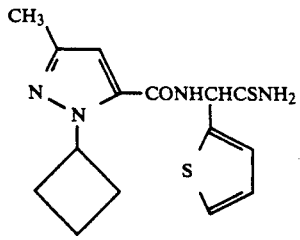

(20)
1-Cyclopentyl-3-methyl-N-[3-furyl-(thiocarbamoyl)-methyl]-1H-pyrazole-5-carboxamide

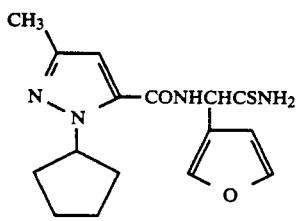

(21)
1-Cyclopentyl-3-methyl-N-[3-thienyl-(thiocarbamoyl)-methyl]-1H-pyrazole-5-carboxamide

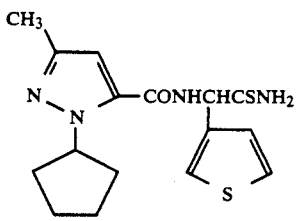

(22)
1-Cyclopentyl-3-methyl-N-[2-furyl-(thiocarbamoyl)-methyl]-1H-pyrazole-5-carboxamide

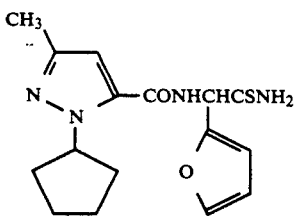

(23)
1-Cyclopentyl-3-methyl-N-[2-thienyl(thiocarbamoyl)-methyl]-1H-pyrazole-5-carboxamide

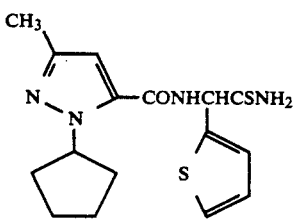

(24)
1-Cyclohexyl-3-methyl-N-[3-furyl-(thiocarbamoyl)-methyl]-1H-pyrazole-5-carboxamide

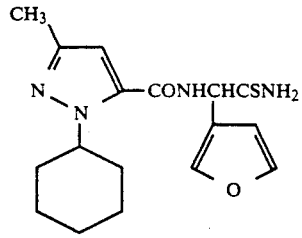

(25)
1-Cyclohexyl-3-methyl-N-[3-thienyl-(thiocarbamoyl)-methyl]-1H-pyrazole-5-carboxamide

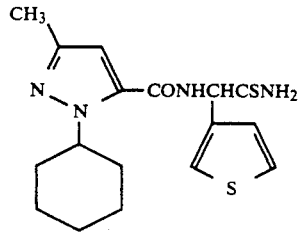

(26)
1-Cyclohexyl-3-methyl-N-[2-furyl(thiocarbamoyl)-methyl]-1H-pyrazole-5-carboxamide

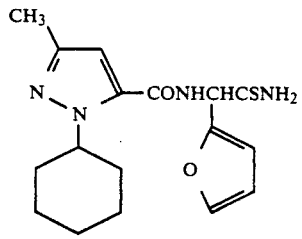

(27)
1-Cyclohexyl-3-methyl-N-[2-thienyl(thiocarbamoyl)-methyl]-1H-pyrazole-5-carboxamide

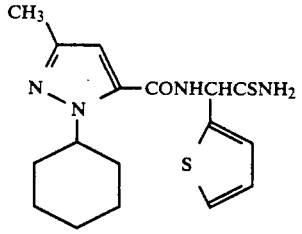

(28)
1-(2,3-epoxypropyl)-3-methyl-N-[3-furyl(thiocarbamoyl)-methyl]-1H-pyrazole-5-carboxamide

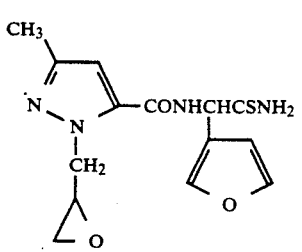

(29)
1-(2,3-epoxypropyl)-3-methyl-N-[3-thienyl(thiocarbamoyl)methyl]-1H-pyrazole-5-carboxamide -continued

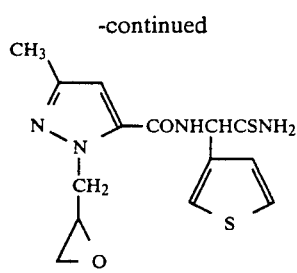

(30)
1-(2,3-epoxypropyl)-3-methyl-N-[2-furyl(thiocarbamoyl)-methyl]-1H-pyrazole-5-carboxamide

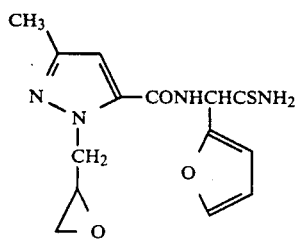

(31)
1-(2,3-epoxypropyl)-3-methyl-N-[2-thienyl(thiocarbamoyl)methyl]-1H-pyrazole-5-carboxamide

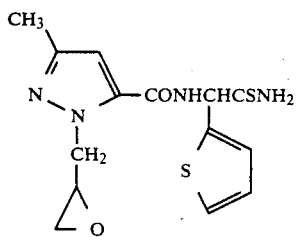

(32)
1-(3-tetrahydrothienyl)-3-methyl-N-[2-furyl(thiocarbamoyl)methyl]-1H-pyrazole-5-carboxamide

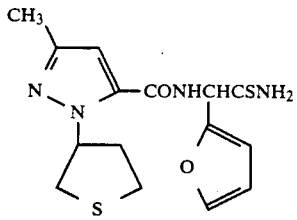

(33)
1-(3-cyclopentenyl)-3-methyl-N-[3-thienyl(thiocarbamoyl)methyl]-1H-pyrazole-5-carboxamide

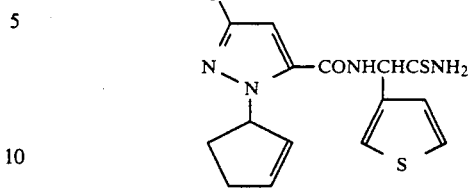

(34)
1-cyclopropyl-3-methyl-N-[2-furyl-(thiocarbamoyl)methyl]-1H-pyrazole-5-carboxamide

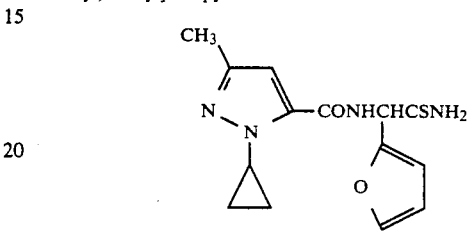

(35)
1-cyclopropyl-3-methyl-N-[2-thienyl-(thiocarbamoyl)methyl]-1H-pyrazole-5-carboxamide

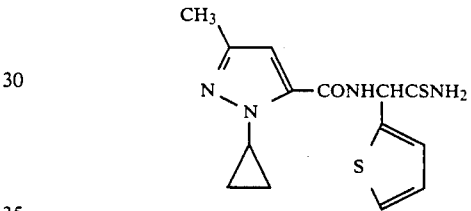

(36)
1-cyclopropyl-3-methyl-N-[3-thienyl-(thiocarbamoyl)methyl]-1H-pyrazole-5-carboxamide

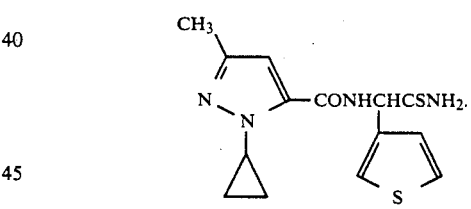

5. A method for inhibiting phytopathogenic fungi of Phycomycetes comprising applying to a living organism a fungicidally effective amount of a compound as claimed in claim 1.

* * * * *